United States Patent
Dahlmann et al.

(10) Patent No.: US 11,136,260 B2
(45) Date of Patent: *Oct. 5, 2021

(54) RADIOPAQUE GLASS AND USE THEREOF

(71) Applicant: SCHOTT AG, Mainz (DE)

(72) Inventors: Ulf Dahlmann, Landshut (DE); Sabine Pichler-Wilhelm, Landshut (DE); Jens Suffner, Landshut (DE); Simone Monika Ritter, Mainz (DE)

(73) Assignee: SCHOTT AG, Mainz (DE)

( * ) Notice: Subject to any disclaimer, the term of this patent is extended or adjusted under 35 U.S.C. 154(b) by 1 day.

This patent is subject to a terminal disclaimer.

(21) Appl. No.: 16/377,270

(22) Filed: Apr. 8, 2019

(65) Prior Publication Data
US 2019/0233325 A1    Aug. 1, 2019

Related U.S. Application Data

(63) Continuation-in-part of application No. 15/658,814, filed on Jul. 25, 2017, now Pat. No. 10,301,212.

(30) Foreign Application Priority Data

Jul. 29, 2016   (DE) .................... 10 2016 114 109.7

(51) Int. Cl.
*C03C 4/08*     (2006.01)
*C03C 3/118*    (2006.01)
(Continued)

(52) U.S. Cl.
CPC ............. *C03C 4/087* (2013.01); *C03C 3/064* (2013.01); *C03C 3/085* (2013.01); *C03C 3/118* (2013.01);
(Continued)

(58) Field of Classification Search
CPC ....... C03C 4/087; C03C 3/064; C03C 4/0021; C03C 3/085; C03C 3/18
See application file for complete search history.

(56) References Cited

U.S. PATENT DOCUMENTS

| 5,340,776 A | 8/1994 | Paschke et al. |
| 5,641,347 A | 6/1997 | Grabowski et al. |

(Continued)

FOREIGN PATENT DOCUMENTS

| DE | 4100604 C1 | 2/1992 |
| DE | 1443173 A1 | 7/1996 |

(Continued)

OTHER PUBLICATIONS

Din 12116 Testing the Resistance of Glass to Attack by Boiling Hydrochloric Acid Solution, and Classification, Mar. 2001, 5 Pages (in English).

(Continued)

*Primary Examiner* — Tae H Yoon

(57) ABSTRACT

The invention relates to a radiopaque glass having a refractive index $n_d$ of 1.480 to 1.561, this glass, apart from impurities at most, being free from SrO and PbO. The glass is based on the $SiO_2$, $Al_2O_3$ and $B_2O_3$ system. The radiopacity can be adjusted using $Cs_2O$ in particular in combination with BaO and/or $SnO_2$ optionally in conjunction with fluorine. The glass may be used in particular as dental glass or as optical glass.

18 Claims, 4 Drawing Sheets

(51) Int. Cl.
  *C03C 3/085* (2006.01)
  *C03C 3/064* (2006.01)
  *C03C 4/12* (2006.01)
  *C03C 4/14* (2006.01)
  *C03C 4/16* (2006.01)
  *A61K 6/77* (2020.01)
  *C03C 4/00* (2006.01)

(52) U.S. Cl.
  CPC .............. *C03C 4/0021* (2013.01); *A61K 6/77* (2020.01); *C03C 2204/00* (2013.01)

(56) References Cited

U.S. PATENT DOCUMENTS

| | | | |
|---|---|---|---|
| 5,976,999 A * | 11/1999 | Evans | C03C 8/20 501/14 |
| 6,121,175 A | 9/2000 | Drescher et al. | |
| 6,297,181 B1 | 10/2001 | Kunert et al. | |
| 6,630,420 B1 | 10/2003 | Naumann et al. | |
| 7,795,164 B2 | 9/2010 | Ritzberger et al. | |
| 7,863,200 B2 | 1/2011 | Leib et al. | |
| 7,895,164 B1 | 2/2011 | Varadarajan et al. | |
| 8,168,693 B2 * | 5/2012 | Ritter | A61K 6/833 523/117 |
| 8,178,595 B2 * | 5/2012 | Ritter | A61K 6/822 523/117 |
| 8,268,065 B2 | 9/2012 | Ritter et al. | |
| 10,301,212 B2 * | 5/2019 | Dahlmann | A61K 6/25 |
| 2005/0054509 A1 | 3/2005 | Hoen et al. | |
| 2005/0277539 A1 | 12/2005 | Assmann et al. | |
| 2007/0184964 A1 | 8/2007 | Peuchert et al. | |
| 2008/0255265 A1 | 10/2008 | Hoescheler et al. | |
| 2009/0298966 A1 | 12/2009 | Vanini et al. | |
| 2010/0210753 A1 | 8/2010 | Ritter et al. | |
| 2010/0210754 A1 | 8/2010 | Ritter et al. | |
| 2011/0218268 A1 | 9/2011 | Ritter et al. | |
| 2014/0106168 A1 * | 4/2014 | Ritter | B32B 17/00 428/392 |

FOREIGN PATENT DOCUMENTS

| | | |
|---|---|---|
| DE | 19849388 A1 | 5/2000 |
| DE | 19945517 A1 | 8/2000 |
| DE | 10222964 A1 | 11/2003 |
| DE | 102005051387 B3 | 1/2007 |
| DE | 102009008951 A1 | 10/2010 |
| DE | 102011084501 B3 | 3/2013 |
| EP | 0885606 A2 | 12/1998 |
| EP | 1547572 A1 | 6/2005 |
| GB | 2251814 A | 7/1992 |
| GB | 2495587 A | 4/2013 |
| GB | 2495587 B | 10/2013 |
| JP | 2000143430 A | 5/2000 |
| JP | 2003026442 A2 | 1/2003 |
| JP | 2004-002062 A | 1/2004 |
| JP | 2005075724 A2 | 3/2005 |
| JP | 2006-513968 A | 4/2006 |
| JP | 2007-526202 A | 9/2007 |
| JP | 2010189262 A | 9/2010 |
| JP | 2011162435 A | 8/2011 |
| KR | 10-2010-0092886 A | 8/2010 |
| KR | 1056099 B1 | 8/2011 |
| WO | 2005060921 A1 | 7/2005 |
| WO | 2007034258 A1 | 3/2007 |
| WO | WO 2012/080513 A1 * | 6/2012 |

OTHER PUBLICATIONS

Din En ISO 4049 Dentistry-Polymer-Based Restorative Materials, Mar. 2010, 34 Pages (in English).
International Standard ISOS 695 Glass-Resistance to Attack by a Boiling Aqueous Solution of Mixed Alkali-Method of Test and Classification, Third Edition, May 15, 1991, 5 Pages (in English).
International Standard ISO 719 Glass-Hydrolytic Resistance of Glass Grains At 98'C—Method of Test and Classification, Second Edition, Oct. 1, 1985, 5 Pages (in English).

* cited by examiner

RADIOPAQUE GLASS AND USE THEREOF

This patent application is a continuation-in-part and claims the priority of U.S. patent application Ser. No. 15/658,814 filed on Jul. 25, 2017, now U.S. Pat. No. 10,301,212, which claims the priority of German Patent Application No. 10 2016 114 109.7 filed on Jul. 29, 2016.

The invention relates to a lead-free radiopaque glass and to the use thereof.

In the dental sector, polymer-based dental compositions are increasingly being used for dental restoration. These polymer-based dental compositions consist customarily of a matrix of organic resins and various inorganic fillers. The inorganic fillers consist predominantly of powders of glasses, (glass-)ceramics, quartz or other crystalline substances (e.g. $YbF_3$), sol-gel materials and/or Aerosils, and are added as filler to the polymer-based composition.

The aim of using polymer-based dental compositions is to prevent possible harmful side-effects of amalgam and also to enhance aesthetics. Depending on the polymer-based dental compositions selected, they may be used for a variety of dental restoration measures, as for example for dental fillings or inlays, onlays, etc., and also for crowns and bridges.

The filler as such is intended on curing to minimize the shrinkage resulting from the polymerization of the resin matrix, and at the same time to increase the abrasion resistance. Where, for example, there is strong adhesion between tooth wall and filling, excessive polymerization shrinkage may result in fracture of the tooth wall. If the adhesion is not sufficient for this purpose, excessive polymerization shrinkage may bring about the formation of marginal gaps between tooth wall and filling, which may promote secondary caries.

Furthermore, certain physical and chemical requirements are imposed on the fillers:

It must be possible for the filler to be processed to give very fine powders. The finer the powder, the more homogeneous is the appearance of the filling. At the same time there is an improvement in the polishability of the filling, leading to improved abrasion resistance, via the reduction in the surface area open to attack, and so to a filling which retains its durability for longer. So that the powders are easy to process, moreover, it is desirable if the powders do not suffer agglomeration.

It is advantageous, furthermore, if the filler is coated with a functionalized silane, since this facilitates the formulation of the dental composition and improves the mechanical properties. The surfaces of the filler particles are customarily covered at least partly with the functionalized silane.

In terms of its transparency and, where appropriate, index of refraction, the dental glass filler should conform as close as possible to the resin matrix. Furthermore, in its entirety, which thus also includes the filler, the polymer-based dental composition is adapted aesthetically to the natural tooth material, to make it as indistinguishable as possible from the surrounding, healthy tooth material. A very small particle size of the powdered filler likewise plays a part with regard to this aesthetic criterion.

Effective chemical resistance of the fillers, especially with regard to water, may make a contribution, furthermore, to a long lifetime of the dental restoration measures.

It is absolutely vital for the treatment of patients, furthermore, that dental restoration measures are visible in an X-ray image. Since the resin matrix is generally invisible in the X-ray image, the fillers have to ensure the necessary X-ray absorption. A filler of this kind which provides adequate absorption of X-rays is referred to as being radiopaque.

Responsible in general for the radiopacity are constituents of the filler, examples being certain components of a glass, or additives. Such additives are also called radiopacifiers. A customary radiopacifier, besides dental glass fillers, is $YbF_3$, which may be added in crystalline, ground form.

According to DIN ISO 4049, the radiopacity of dental glasses or dental materials is reported, relative to the X-ray absorption of aluminium, as the aluminium equivalent thickness (ALET). A relative ALET is based on a sample thickness of 2 mm. The relative ALET of 200%, therefore, means that a glass plate having plane-parallel surfaces with a thickness of 2 mm produces the same attenuation of X-rays as an aluminium plate with a thickness of 4 mm. Analogously, a relative ALET of 500% means that a glass plate having plane-parallel surfaces of 2 mm in thickness produces the same attenuation of X-rays as an aluminium plate 10 mm thick. Below, the radiopacity of the glasses is reported by statements of the relative ALET (in %).

Because the polymer-based dental composition in the application is customarily introduced from cartridges into cavities, where it is modelled, it is intended frequently to be thixotropic in the uncured state. This means that its viscosity decreases when pressure is exerted, whereas without exposure to pressure it is dimensionally stable.

With regard to the filling materials, the inert compositions are distinguished from the reactive dental compositions. The reactive dental compositions include the dental cements. In the case of dental cements, examples being glass ionomer cements, the chemical reaction of the fillers with the organic acid leads to the curing of the dental composition, meaning that the curing properties of the dental composition and thus its workability are influenced by the reactivity of the fillers. The process involved here is often one of setting, which may be preceded by a superficial radical curing, under the action of UV light, for example. The glass here may serve as a filler, which triggers or participates in the chemical reaction, or else as an inert additive which is not involved in the reaction. In that case the chemical reaction is determined by further fillers likewise present in the glass ionomer cement.

Aside from the pure inert fillers and the pure reactive fillers, there are various intermediate stages, which cannot be listed here in detail. As examples of the intermediate stages, mention may be made of "compomers" and "resin modified glass ionomer cement" (RMGIC).

Composites, also called filling composites, in contrast, contain further fillers which in chemical terms are largely inert, since their curing characteristics are determined by constituents of the resin matrix, being therefore determined initially, and a chemical reaction of the fillers and/or additives is often undesired here.

Since on the basis of their different compositions glasses represent a class of material having diverse properties, they are frequently employed as fillers for polymer-based dental compositions. Applications other than as dental material, either in pure form or as a component of a materials mixture, are also possible, as for example for inlays, onlays, facing material for crowns and bridges, material for artificial teeth or other material for prosthetic, preservative and/or preventive tooth treatment. In their application as dental material, such glasses are referred to generally as dental glasses.

Another desirable property of the dental glass, in addition to those described above, is freedom from lead oxide (PbO), which is toxic.

Dental glasses therefore represent particularly high-grade glasses. Such glasses may likewise be employed in optical applications, especially where the application profits from the radiopacity of the glass. Because the radiopacity means that the glass absorbs electromagnetic radiation in the region of the X-ray spectrum, such glasses are at the same time filters for X-radiation. Sensitive electronic components may be damaged by X-radiation. In the case of electronic image sensors, for example, the passage of an X-ray quantum may damage the corresponding region of the sensor or may lead to an unwanted sensor signal which can be perceived, for example, as image interference and/or noisy pixels. For certain applications therefore it is necessary, or at least advantageous, for the electronic components to be protected from X-radiation, by filtering out such radiation from the spectrum of the incident radiation, using corresponding glasses.

Numerous dental glasses and other optical glasses having similar optical position or comparable chemical composition are described in the prior art, but these glasses exhibit considerable disadvantages in production and/or in use. In particular, many of the glasses contain sizeable proportions of fluorides and/or $Li_2O$, which evaporate very readily during melting and fusing, thereby complicating the precise establishment of the glass's composition.

Chemically inert, barium-free dental glasses for use as a filler in composites are subject matter of DE 198 49 388 A1. In the case of the low-index glasses, the glasses proposed therein necessarily include proportions of ZnO and F. The latter proportions may lead to reactions with the resin matrix, which may in turn have consequences for its polymerization behaviour. Moreover, the $SiO_2$ proportion, at 20-45 wt %, is limited to allow the glass described to include sufficient radiopacifier and F. In particular, in the case of low ZnO and $ZrO_2$ contents, the addition of up to 27 wt % of SrO is recommended.

WO2005/060921 A1 describes a glass filler which is to be suitable particularly for dental composites. It contains 9 to 20 mol % of alkali metal oxides. The objective in that specification is to provide glass particles whose concentration of alkali metal ions is lower at the edge of the particles than in their centre. This means that the glasses described have a deliberate chemical instability, since otherwise it would not be possible to attain this concentration behaviour. It can be assumed that the necessarily low chemical stability is achieved by the stated proportions of the alkali metals in the original glass.

An alkali metal silicate glass serving as a filler for dental material is described in EP 0885606 B1. In the glass, which is of high $SiO_2$ content, the $Al_2O_3$ proportion of at least 5 wt % raises the viscosity and so leads to very high melting temperatures. Sodium oxides and potassium oxides are included as mandatory components. Moreover, the glass contains no components giving it radiopacity.

DE 4443173 A1 comprises a barium-free glass of high zirconium content, having a $ZrO_2$ content of more than 12 wt %, and other oxides. Such fillers are too reactive, especially for modern dental compositions based, for example, on acrylate, with which excessively rapid, uncontrolled curing can occur. Zirconium oxide in this quantity has a tendency towards devitrification. It produces phase separation, possibly with nucleation and subsequent crystallization. Moreover, such glasses can only be produced with high alkali metal contents, in order to ensure not too high a melting temperature, which would overstrain the melting assemblies. In turn, however, such high contents of alkali metal are deleterious to the chemical stability of the glasses.

DE 199 45 517 A1 likewise describes a glass of high zirconium content which, in applications in the dental sector, displays the same problems as the glasses in the aforementioned specification.

DE 10 2005 051 387 B3 describes as dental glass a magnesium aluminosilicate glass which in order to achieve radiopacity and an index of refraction of 1.50 to 1.549, has high contents of $La_2O_3$ and/or $Y_2O_3$ and also $WO_3$ and $ZrO_2$. This glass is free from barium, strontium and alkali metal oxides. In view of the high magnesium oxide content of such glasses, they tend towards phase separation. Another disadvantage is the high crystallization susceptibility, owing to the contents of $WO_3$ and $ZrO_2$. These contents additionally raise the melting temperatures. $La_2O_3$ is a very costly raw material and ought therefore to be avoided.

DE 10 2009 008 951 A1 discloses a radiopaque, barium-free glass and the use thereof as dental glass, mandatorily containing zirconium oxide. In order to achieve a narrow index of refraction range of 1.518 to 1.533, $ZrO_2$ is used with $Cs_2O$ and/or $La_2O_3$. In order that such glasses can be melted, furthermore, a high $K_2O$ proportion is required. Here again, a problem with such glasses is the crystallization tendency in combination with the relatively high melting temperatures and the raw materials costs occasioned by the $La_2O_3$ used. Glasses with low indices of refraction are not described by this prior art.

DE 10 2011 084 501 B3 discloses a barium-free, radiopaque glass having an index of refraction of 1.50 to 1.58. The glass is based on a combination of SrO and $La_2O_3$ and $ZrO_2$ as radiopacifier. Furthermore, $Cs_2O$ may be added to increase the radiopacity. Disadvantages of these glasses are the high melting temperatures and the crystallization tendency. $La_2O_3$, as described above, is very expensive.

JP 2004-002062 A discloses a glass substrate for flat screens. Besides SrO, the glasses disclosed contain primarily BaO and also high proportions of $Al_2O_3$ and MgO. The $Al_2O_3$, SrO, BaO and MgO components are needed as network transformers in order to ensure the meltability of the glass. These glasses as well are not contemplated for use as dental glasses, since they lack by far the requisite radiopacity. Apart from that, the content of $Al_2O_3$ raises the viscosity of the high-$SiO_2$-content glass and therefore necessitates high melting temperatures for the purpose of production. High contents of MgO are a disadvantage in glasses for dental applications, which are intended to have low indices of refraction in conjunction with high radiopacity. MgO does not raise the radiopacity to the same extent as the other alkaline earth metal oxides CaO, SrO and BaO, instead being manifested primarily in an increase in the index of refraction $n_d$, and it may therefore complicate the desired balance between low index of refraction and high radiopacity.

Features shared by all of the glasses identified in the prior art are that they either have low hydrolytic resistance or are too reactive and/or are not radiopaque, or they include components harmful to health and/or the environment. Many known dental glasses, moreover, contain SrO, which greatly increases the melting temperature. In addition to this economic disadvantage, a high SrO proportion makes for difficult-to-control crystallization operations during the production process of numerous glasses. It has emerged, moreover, that with the known radiopacifiers, employed alone or in the known combinations (usually in combination with $La_2O_3$), the radiopacity achievable cannot be increased arbitrarily and satisfactorily without too great an increase in the refractive index. Glasses having a refractive index of greater than 1.65 can currently not be used satisfactorily in practice (as described in WO 2007/034258 A1, for example) as dental glasses, fillers for polymer-based dental compositions, etc. A disadvantage of lanthanum oxide, moreover, is that it is highly priced, so reducing the economics of the glasses produced using it.

It is an object of the invention to provide a lead-free, radiopaque glass of relatively low refractive index, having an improved radiopacity.

In particular, it is also an object of the invention, for improved ease of production, to provide a glass system with which it is possible, within a given refractive index range, to produce glasses having a precisely defined index of refraction and, with regard to the index of refraction, improved radiopacity more easily. The glass is to be suitable preferably for use in the medical sector, especially in the dental sector as dental glass, and as optical glass. It is to be rationally producible and nevertheless of high-grade and biocompatible, and also to be suitable for passive and active dental protection, and is to have excellent properties in terms of processability, the setting behaviour of surrounding polymer matrices, and also the long-term stability and the strength. In order to meet the requirements in modern dental treatment and dental technology, moreover, the glass according to the invention must have at least good hydrolytic stability.

The glass according to the invention in its basic matrix, furthermore, is to be free from colouring components such as $Fe_2O_3$, CoO, NiO, CuO etc., for example, apart from impurities at most or importations and/or residual constituents that are difficult to avoid in industrial production, in order so to enable an optimum starting colour location for possible adaptations to the tooth colour and/or, in the case of optical applications, to enable the adaptation of the spectrum of the electromagnetic radiation that passes through. Moreover, the glass is to be free from a second glass phase and/or from colouring particles which lead to scattering and likewise modify the perceived colour. One or more further glass phases would lower the resistance of the glass.

The object is achieved by the glass according to the independent claims. Preferred embodiments and applications are apparent from the dependent claims.

Provided in particular is a radiopaque glass, being free from PbO apart from impurities at most, wherein the glass has a refractive index $n_d$ in the refractive index range between 1.480 and 1.561 and has a relative aluminium equivalent thickness ALET (%) which is greater than or equal to a minimum relative aluminium equivalent thickness (min. relative ALET) which is determined by the following equation:

min. relative ALET (%)=$C*n_d$-$D$, where $C$=11000 and $D$=16160.

Provided in particular is a radiopaque glass having a refractive index $n_d$ of 1.480 to 1.561, being free from PbO apart from impurities at most, wherein the assignment between the refractive index $n_d$ of the glass and the relative aluminium equivalent thickness ALET (%) is as follows:

| $n_d$ | ALET min. | ALET max. |
|---|---|---|
| 1.480 to <1.490 | 120% | 700% |
| 1.490 to <1.510 | 260% | 1000% |
| 1.510 to <1.530 | 520% | 1200% |
| 1.530 to <1.550 | 780% | 1500% |
| 1.550 to 1.561 | 850% | 1600% |

Provided in particular is a radiopaque glass having a refractive index $n_d$ of 1.480 to 1.561, being free from PbO apart from impurities at most, wherein the assignment between the refractive index $n_d$ of the glass and the relative aluminium equivalent thickness ALET (%) is as follows:

| $n_d$ | ALET min. | ALET max. |
|---|---|---|
| 1.480 to <1.490 | 120% | 760% |
| 1.490 to <1.500 | 240% | 875% |
| 1.500 to <1.510 | 360% | 1000% |
| 1.510 to <1.520 | 475% | 1105% |
| 1.520 to <1.530 | 590% | 1220% |
| 1.530 to <1.540 | 705% | 1335% |
| 1.540 to <1.550 | 820% | 1500% |
| 1.550 to 1.561 | 850% | 1600% |

In some embodiments, the radiopaque glass comprises (in wt % based on oxide)

| | |
|---|---|
| $SiO_2$ | 35-75 |
| $B_2O_3$ | 2-16 |
| $Al_2O_3$ | 0.8-7.5 |
| $K_2O$ | 0-14 |
| BaO | 0-24 |
| $Cs_2O$ | 1-30 |
| $SnO_2$ | 0-15 |
| F | 0-8 |
| BaO + $Cs_2O$ + $SnO_2$ + F | ≥10. |

$Cs_2O$ is usually present in the glass acting as radiopacifier. In advantageous embodiments, it ensures in combination with at least one further radiopacifier the high radiopacity of the glass. Particularly advantageous variants contain $Cs_2O$ and at least BaO or $SnO_2$ as radiopacifiers, wherein $La_2O_3$ can also be comprised optionally. The advantageous $SnO_2$-containing radiopaque glasses can comprise $SnO_2$ besides $Cs_2O$ and BaO, optionally together with $La_2O_3$. A further advantageous embodiment comprises the combination of $Cs_2O$ and $La_2O_3$ serving as radiopaque components, wherein an advantageous variant of this embodiment can be free from BaO.

Some advantageous variants of the mentioned radiopaque glasses can contain fluorine (fluorine-containing variants). The component fluorine can adjust the refractive index depending on the used radiopacifiers. If fluorine is contained, the content can be ≥0.3 wt, preferably ≥0.5 wt. %. A preferred upper limit can be 6 wt. %, advantageously 5.5 wt. %, preferably 2.5 wt. %. Other advantageous variants have a significantly reduced fluorine content with a range of 0 to <0.3 wt %, i.e. such variants can be poor in fluorine (fluorine-poor variants) or are even free of fluorine (fluorine-free variants).

An advantageous fluorine-containing embodiment of the invention comprises (in wt % based on oxide)

| | |
|---|---|
| $SiO_2$ | 35-75 |
| $B_2O_3$ | 4-15, in particular 5-15 |
| $Al_2O_3$ | 0.8-7.5 |
| $K_2O$ | 0-10 |
| BaO | 0.6-24 |
| $Cs_2O$ | 1-30 |
| $SnO_2$ | 0-15, in particular 1-15 |
| F | ≥0.3, in particular ≥0.5 |
| BaO + $Cs_2O$ + $SnO_2$ + F | ≥10 |

In the purpose of the invention, advantageous sub-variants of the fluorine-containing variant are possible, i.e. a $SnO_2$-containing advantageous sub-variant and a $SnO_2$-free advantageous sub-variant. The advantageous $SnO_2$-containing sub-variant comprises $SnO_2$, advantageously with a content of >0-15 wt %, preferably 0.3-15 wt % or 0.5-15 wt %, further advantageously 1-15 wt %. Another advantageous $SnO_2$ content is >4-15 wt %. Alternatively, the fluorine-containing radiopaque glasses can advantageously be $SnO_2$-free ($SnO_2$ free sub-variant).

An advantageous fluorine-reduced embodiment (fluorine-poor or fluorine-free variant) of the invention is a radiopaque glass comprising (in wt % based on oxide)

| | |
|---|---|
| $SiO_2$ | 35-75 |
| $B_2O_3$ | 4-15, in particular 5-15 |
| $Al_2O_3$ | 0.8-7.5 |
| $K_2O$ | 0-10 |
| BaO | 0-24, in particular 0.6-24 |
| $Cs_2O$ | 1-30 |
| $SnO_2$ | 0-15 |
| F | 0 < 0.3 |
| $BaO + Cs_2O + SnO_2 + F$ | ≥10 |

In the purpose of the invention, advantageous sub-variants of the fluorine-reduced variants are possible, i.e. a $SnO_2$-containing advantageous sub-variant and a $SnO_2$-free advantageous sub-variant. The advantageous $SnO_2$-containing sub-variant comprises $SnO_2$, advantageously with a content of >0-15 wt %, preferably 0.3-15 wt % or 0.5-15 wt %, further advantageously 1-15 wt %. Another advantageous $SnO_2$ content is >4-15 wt %. Alternatively, the fluorine-poor and/or fluorine-free radiopaque glasses can advantageously be $SnO_2$-free ($SnO_2$ free sub-variant).

The glass according to the invention can have a refractive index $n_d$ (also called index of refraction) of 1.480 to 1.561. It is therefore very well adapted to the available dental polymers and/or acrylate-based resins in this refractive index range, thereby satisfying the aesthetic requirements imposed on a polymer-based dental composition, especially on a dental glass/polymer composite, for appearance to be natural.

The glass according to the invention achieves the properties of lead-containing dental glasses in relation to the requisite X-ray absorption without using lead or other substances objectionable on health grounds. The glass according to the invention can be lead-free. The term "free from" in this context denotes an absence of these substances apart from unavoidable contamination at most, that may be caused, for example, by air contamination and/or impurity in raw materials employed. However, even contamination of the glass with the unwanted substances is in general not to exceed 300 ppm for $Fe_2O_3$, preferably not more than 100 ppm, 30 ppm for PbO, 20 ppm for $As_2O_3$, 20 ppm for $Sb_2O_3$, and 100 ppm for other impurities, especially in dental glasses. SrO is always closely associated with the BaO in the raw material. Depending on the purity of the BaO raw material, there may be up to 0.7 wt % of SrO in the glass according to the invention. These limits are embraced by the wording "apart from impurities at most, free from". Particularly preferred, of course, is the complete absence of the stated unwanted substances from the glass according to the invention. No SrO component is actively added, preferably, to the glass according to the invention.

The X-ray absorption and therefore the radiopacity can be advantageously achieved through a combination of radiopacifiers.

According to an advantageous variant of the invention, radiopacity can be achieved by the combination of $Cs_2O$, BaO and/or $SnO_2$, such as for example through the presence of at least two of these components, advantageously through the presence of these three components. Unlike earlier dental glasses, which attempted to achieve radiopacity usually through the high content of, as far as possible, one high absorbing component, or through a combination with $La_2O_3$, the radiopacity in accordance with these variants of the invention can be achieved by the appropriate combination of at least two of these BaO, $SnO_2$ and/or $Cs_2O$ components, which are effective for the radiopacity. In this way it is possible to attain the particularly stringent requirements for the optical properties of the glass, and also to achieve the very good hydrolytic and/or chemical resistance. Preferred for the content of BaO, $SnO_2$ and $Cs_2O$ are in total at least 8 wt %, more preferably at least 10 wt %, very preferably at least 12 wt %. Too little of these components can lead to insufficient X-ray absorption. The higher the sum of these radiopacifiers in the glass, the higher is the radiopacity as well. An advantageous upper limit for the sum of BaO, $SnO_2$ and $Cs_2O$ may be 51 wt %, preferably 49 wt %, more preferably 47 wt %, also preferably 45 wt %, further preferably 43 wt %.

Furthermore regarding especially the fluorine-containing advantageous variants, the radiopaque glass comprises a defined amount of fluorine, serving to specifically adjust the refractive index of the glass depending on the particular amount of radiopacifiers. This counteracts the effect whereby, as a result of using a larger quantity of radiopacifier in the glass, the radiopacity is indeed increased, but at the same time the refractive index of the resulting glasses goes up. Through the addition of fluorine it is possible to maintain within limits the increase in the refractive index, or even to prevent the increase in the refractive index.

The combination of the radiopacifying components BaO, $Cs_2O$, and/or $SnO_2$ optionally with F has proved, surprisingly, to be particularly suitable for creating glasses which have a high radiopacity in the relatively wide refractive index range from 1.480 to 1.561. In the context of the invention, provision can be made for this purpose for the sum of BaO, $Cs_2O$, $SnO_2$ and F in wt % based on oxide to be at least 8 wt. % or at least 9 wt %, preferably at least 10 wt %. Advantageously the sum can be at least 11 wt % or at least 12 wt %, some advantageous variants can have at least 13 wt % or at least 14 wt % for the sum, other advantageous variants can have at least 15 wt % or at least 16 wt. % or at least 17 wt % for the sum. An advantageous upper limit for the sum of BaO, $Cs_2O$, $SnO_2$ and F may be 56 wt %, preferably 54 wt %, more preferably 52 wt %, also preferably 50 wt %, further preferably 48 wt %. Some advantageous variants can have an upper limit of 42 wt % or 36 wt % or 35 wt % for the sum. It is common knowledge that glasses having a lower index of refraction tend to be able to achieve a lower radiopacity and correspondingly lower values of aluminium equivalent thickness than glasses having a higher index of refraction. The reason for this is that for low-index glasses only relatively low amounts of radiopacifiers can be used. If the proportion of the radiopacifiers were increased, the refractive index would shift to higher values. Through the advantageous combination of BaO, $Cs_2O$, and $SnO_2$ in particular with F it is possible to shift the radiopacity of the glasses and, correspondingly, the aluminium equivalent thickness to higher values over the whole refractive index range according to the invention. This means that for a given index of refraction, it is possible to achieve substantially higher X-ray visibility values than was hitherto possible. It is possible, moreover, to specifically adjust the index of refraction in a radiopaque glass.

A particularly advantageous embodiment of a radiopaque glass having fluorine and an advantageous combination of three radiopacifiers comprises:

| | |
|---|---|
| $SiO_2$ | 38-70 |
| $B_2O_3$ | 6-15 |
| $Al_2O_3$ | 1-7 |
| $K_2O$ | 0-7 |
| BaO | 0.8-20 |
| $Cs_2O$ | 1-28 |
| $SnO_2$ | 1-15, preferably >4-15 |
| F | 0.75-2.5 |
| BaO + $Cs_2O$ + $SnO_2$ + F | ≥10 |

All in all, success has been achieved with the invention in providing a glass system which allows the refractive index of the glass to be precisely adjusted to the particular requirements by varying the proportions of the components within the stated system, wherein the glass has an improved radiopacity for a given refractive index. This simplifies the production of differently refracting glasses with high radiopacity.

Below the glass components are described for all glasses according to the invention and advantageous variants:

As a basis, the glass according to the invention can comprise $SiO_2$ with a proportion of 35 to 75 wt % as glass-forming component. The upper limit in accordance with the invention can be 75 wt %. Higher contents of $SiO_2$ may lead to disadvantageously high melting temperatures, whereas, moreover, the requisite radiopacity might not be achieved. In the case of advantageous embodiments, 73 wt %, preferably 70 wt %, more preferably 68.5 wt % or 65 wt % may be selected as an $SiO_2$ upper limit. Some advantageous variants have an $SiO_2$ upper limit of 64 wt %, advantageously 61 wt % or 59 wt % or 56 wt % or 53 wt %. In accordance with the invention, the lower limit can be 35 wt %. Lower contents may have adverse consequences for the chemical resistance and the devitrification tendency. The $SiO_2$ lower limit in the case of an advantageous glass composition may be 36 wt %, preferably 37 wt %, more preferably 38 wt %, further preferably 39 wt %. Some advantageous variants can comprise at least 40 wt %, preferably at least 42 wt % or at least 45 wt % or at least 47 wt % or at least 50 wt % of $SiO_2$. One preferred embodiment of the glass according to the invention envisages a $SiO_2$ content of 38 to 70 wt % and more preferably of 39 to 70 wt %.

$B_2O_3$ can be provided in the glass according to the invention with a content of 2 to 16 wt %, advantageously of 4 to 15 wt %, preferably of 5 to 15 wt %. It may be present advantageously in the range from 6 to 15 wt % or 7 to 15 wt %. Some advantageous variants comprise 3 to 14 wt % of this component. $B_2O_3$ has a positive influence on glass formation and on melting behaviour. It also acts as a flux. Apart from the lowering effect on the melting temperature, the use of $B_2O_3$ leads at the same time to an improvement in the crystallization stability of the glass according to the invention. In accordance with the invention, therefore, the lower limit can be 2 wt %. For certain glasses, 3 wt % or 4 wt %, advantageously 5 wt %, preferably 6 wt %, preferably 7 wt %, may also be selected as an advantageous lower limit for boron oxide. The upper limit for boron oxide in accordance with the invention can be 16 wt %, preferably 15 wt %. Higher proportions are not recommended in this system, so as not to jeopardise the chemical resistance. A maximum of 14.5 wt %, preferably a maximum of 14 wt %, of boron oxide may also advantageously be included. If contents of $B_2O_3$ are too high, there may be instances of separation in the glass, which in turn represent an unwanted inhomogeneity of refractive index and, moreover, have adverse effects on the chemical resistance.

The glass according to the invention can include $Al_2O_3$ in the range from 0.8 to 7.5 wt %. It may be present advantageously in the range from 0.8 to 6 wt % or 1 to 7 wt %. $Al_2O_3$ improves the chemical resistance of the glass. In accordance with the invention, therefore, it can be present at not less than 0.8 wt % in the glass.

At least 1 wt %, preferably at least 1.2 wt % of aluminium oxide may also advantageously be used. However, an $Al_2O_3$ content of around 7.5 wt % ought not to be exceeded, so as not to increase the viscosity of the glass—especially in the hot processing area—to such an extent that the glass is difficult to melt. Moreover, excessively large amounts of aluminium oxide can impair the devitrification tendency and also the resistance of the glass towards acids. The upper limit of $Al_2O_3$ is preferably 7 wt %, more preferably indeed just 6.5 wt % or 6 wt %.

Alkali metal oxides from the group of $Li_2O$, $Na_2O$ and $K_2O$ may be needed in order for the glass to be able to be melted at all. $K_2O$ serves for adjustment of the melting temperatures and at the same time strengthens the glass network. In accordance with the invention, therefore, it can be present with a proportion of 0 to 14 wt %, advantageously of 0 to 12 wt %, preferably of 0 to 10 wt % in the glass composition. For $K_2O$ the range from 0 to 7 wt % can be preferred, from 0 to 5 wt % can be particularly preferred for some advantageous variants. The upper limit of 14 wt % for $K_2O$ in accordance with the invention ought not to be exceeded, since the content of alkali metal oxides lowers the chemical resistance. Advantageously, also 12 wt % or 11 wt %, preferably 10 wt %, preferably 7 wt % preferably 6 wt % may be selected as an upper limit. Particularly advantageous variants comprise at most 5 wt %, more preferably at most 4 wt % of $K_2O$. For some advantageous variants an advantageous lower limit for $K_2O$ can be 0.5 wt %, 1 wt %, 1.5 wt % or 2 wt %. Embodiments that are free of $K_2O$ are also possible in the purpose of the invention.

Sodium ions and lithium ions have a small size which renders them more readily leached out of the glass matrix, thereby diminishing the chemical resistance, especially the hydrolytic resistance. In one advantageous embodiment of the invention, the radiopaque glass is free from $Na_2O$ and/or $Li_2O$ apart from impurities at most.

Impurities may be introduced into the glass by contamination of the raw materials used for glass production, and/or by contamination and/or corrosion of the melting assemblies employed. Such impurities generally do not exceed a proportion of 0.2 wt %, especially 0.1 wt %. This also, of course, includes the complete absence of the component in question. "Free from a component" therefore means that the glass essentially does not contain this component, i.e. that any such component is present as an impurity at most in the glass, but is not added as an individual component to the glass composition.

The content of barium oxide can be 0 to 24 wt %, preferably 0.6 to 24 wt %. A preferred range is that from 0.8 to 20 wt %, more preferably for some variants from 1 to 18.5 wt %. Too high an amount of BaO can lead to the deterioration of the chemical resistance. The upper limit of 24 wt % ought therefore not to be exceeded. As an upper limit it is also possible to select for some variants, advantageously, 22 wt % or 21 wt %, more advantageously 20 wt %, preferably 18.5 wt % or 18 wt %. Further advantageous upper limits can be 17 wt %, 15 wt %, 14 wt %, 12 wt % or 10 wt %. In advantageous variants at least there ought to be 0.6 wt % of BaO present in the glass, in order to acquire, together with the other substances, the X-ray absorption. BaO may be present in the glass advantageously at not less than 0.8 wt %, preferably not less than 1 wt %, more preferably not less than 1.1 wt %. Some advantageous variants can have a lower limit of BaO of 2 wt %, 4 wt % or 6 wt %. However, BaO-free radiopaque glass variants are also possible in the context of the invention which are described now.

Advantageous embodiments of radiopaque glasses can be free of BaO. In such glasses radiopacity can be based on $Cs_2O$ only. For producing a higher X-ray absorption, $La_2O_3$ and/or $SnO_2$ can advantageously be used in the glass as radiopacifier(s) in addition to the contained $Cs_2O$. Advantageous variants of a radiopaque glass having a refractive index $n_d$ of 1.480 to 1.561, being free from PbO and BaO apart from impurities at most, can comprise (in wt % based on oxide)

| | |
|---|---|
| $SiO_2$ | 35-75, in particular 38-70 |
| $B_2O_3$ | 2-16, in particular 5-15, preferably 6-15 |
| $Al_2O_3$ | 0.8-7.5, in particular 0.8-6 |
| $K_2O$ | 0-14, in particular 0-10, preferably 0-7 |
| $Cs_2O$ | 1-30, in particular 6-28, preferably 7-24 |
| $SnO_2$ | 0-15, in particular 0-6, preferably 0-3 |
| F | 0-8, in particular 0-6, preferably 0-3 |
| $La_2O_3$ | 0-19, in particular 0-16 |
| $BaO + Cs_2O + SnO_2 + F$ | ≥10. |

Regarding the BaO-free variants the component $Cs_2O$ or a combination of $Cs_2O$ and $La_2O_3$ and/or $SnO_2$ acting as radiopacifiers can be sufficient in order to produce the radiopacity wanted in the desired refractive index range. For glasses in medical applications, especially in the dental area BaO-free variants are an advantageous alternative to the known BaO-containing and/or SrO-containing radiopaque glasses. Advantageously BaO-free variants also have a low fluorine content, especially of less than 2 wt %, preferably of less than 1 wt % or less than 0.5 wt % or less than 0.3 wt. %. Advantageous BaO-free embodiments can also be free of fluorine.

$Cs_2O$ in accordance with the invention can be likewise used to establish the X-ray visibility, but at the same time also contributes to improving the meltability. In accordance with the invention, $Cs_2O$ can be present in the glass composition at 1 to 30 wt %, preferably 1 to 28 wt %, more preferably 1.5 to 26 wt %, and very preferably 2 to 25 wt %. The alkali metal Cs is more immobile in a glass matrix by comparison with the alkali metals Li, Na, K and Rb. It is therefore leached less severely and so detracts less from the chemical resistance than do the aforementioned alkali metals. Since too small an amount of $Cs_2O$ can result in poorer X-ray visibility and increased melting temperatures, the lower limit according to the invention can be 1 wt %. In the case of an advantageous glass composition, the lower limit may also be 1.5 wt %, more advantageously 2 wt %, preferably 2.5 wt %, very preferably 3 wt %. Some advantageous variants can contain at least 5 wt % or at least 6 wt % or at least 7 wt % $Cs_2O$. Other advantageous variants can have a lower limit for $Cs_2O$ of 9 wt % or 10 wt %. In accordance with the invention there ought to be not more than 30 wt % of $Cs_2O$ present, since otherwise the chemical resistance is impaired. An advantageous glass composition contains not more than 28 wt % of $Cs_2O$, preferably not more than 26 wt % of $Cs_2O$, more preferably not more than 25 wt % or not more than 24 wt % of $Cs_2O$. Some advantageous variants can contain at most 22 wt %, preferably at most 20 wt % or at most 19 wt % of $Cs_2O$.

$SnO_2$ can advantageously serve likewise for adjusting the X-ray visibility. It contributes to a high radiopacity, with the index of refraction being increased less strongly than in the case of other radiopacifiers. This component can be present in the glass composition with a proportion of 0 to 15 wt %. Some advantageous variants of the glasses according to the invention are $SnO_2$-free.

In $SnO_2$-containing variants $SnO_2$ can be present in the glass composition with an advantageous proportion of 0.5 to 15 wt %, advantageously of 1 to 15 wt %, advantageously 3 to 15 wt %, preferably 4 to 15 wt %, more preferably >4 to 15 wt %, very preferably 4 to 12 wt %, especially preferably 4-10 wt %. Too small an amount of $SnO_2$ may lead to poor X-ray visibility, and so this component ought to be present at not less than 0.1 wt % or 0.3 wt %, advantageously not less than 0.5 wt % or not less than 1 wt % referring to the $SnO_2$-containing advantageous variants. Moreover, $SnO_2$ improves and secures the chemical resistance of the $Cs_2O$-containing glass. As an $SnO_2$ lower limit, 3 wt %, preferably 4 wt %, more preferably >4 wt % may advantageously also be provided. Too high an amount of $SnO_2$ can result in severe devitrification and/or crystallization tendency. The upper limit of 15 wt % ought therefore not to be exceeded. Selected as an upper limit there may also be, advantageously, 13 wt %, preferably 12 wt %, more preferably 10 wt %, very preferably also 9 wt % of $SnO_2$. Variants having less $SnO_2$ may have an advantageous upper limit of 6 wt % or 3 wt %.

In the context of the advantageous fluorine-containing variants of the invention, the radiopaque glass can contain fluorine with a proportion of at least 0.3 wt %, preferably at least 0.5 wt %. Present advantageously are at most 8 wt %, preferably at most 5.5 wt %, preferably at most 5 wt. % or—for some variants—at most 2.5 wt % of fluorine. Some variants have an upper limit for F of 6 wt % or 3 wt %. Advantageous ranges for F in advantageous embodiments may also be 0.75 to 2.5 wt %, particularly advantageously from 0.75 to 2.25 wt %, preferably 1 to 2 wt %. Fluorine here is reported in atomic form, referred to the mass, in the composition. It serves for adjusting the refractive index in interaction with the above-described combination of radiopacifiers, and improves the melting characteristics of the glass batch by lowering the melting temperatures. It may therefore be included at not less than 0.3 wt %, preferably at not less than 0.5 wt % in the composition. 0.75 wt % as well, preferably 1 wt %, may be selected as an advantageous lower limit. The upper limit of 8 wt %, advantageously 6 wt %, preferably 5.5 wt %, preferably 5 wt % ought not to be exceeded, since otherwise the component may evaporate during the melting operation and there may be an inhomogeneous distribution of index of refraction in the glass. Fluorine may also advantageously be present with a proportion of at most 2.5 wt %, preferably at most 2.25 wt %, more preferably at most 2 wt % in some variants.

In the fluorine-poor variants of the invention less than 0.3 wt % of F can be present. The fluorine-free variants are free of F.

At this point it may be noted that, in a manner evident to the skilled person and embraced by the present description, any of the stated upper and/or lower limits of one component may be combined arbitrarily with every stated upper and/or lower limit of another component.

In one advantageous embodiment of the glass of a corresponding variant comprising $SnO_2$ and F, provision is made for the molar ratio of $SnO_2$ to F to be at least 0.4, preferably at least 0.45, more preferably at least 0.49, very preferably at least 0.5. The molar ratio of $SnO_2$ to F in the advantageous embodiment is at most 0.85, preferably at most 0.79, more preferably at most 0.77, with further preference at most 0.75, also preferably at most 0.72, very preferably at most 0.7. Through this measure it is possible to set the index of refraction of the glass precisely in conjunction with a relatively high X-ray absorption. A further advantage is that the precise ratio ensures the meltability of the glass. Too high a value results in inhomogeneous melts.

In order to improve further the adjustment of index of refraction and radiopacity, i.e. high aluminium equivalent thickness, in the radiopaque glass, it is advantageous if the molar ratio of $Cs_2O$ to the sum of the above-stated opacifiers $Cs_2O$, BaO and $SnO_2$ is at least 0.05, preferably at least 0.07, more preferably at least 0.1. It is advantageous not to exceed an upper limit of 0.48, preferably of 0.45, more preferably of 0.41. Too small a ratio leads to too low X-ray absorption. Too high a ratio reduces the chemical resistance.

The radiopaque glass may optionally contain $ZrO_2$ with a proportion of 0 to 2 wt %, preferably 0 to 1 wt %. This zirconium content improves the mechanical properties, and particularly the tensile strength and compressive strength, and also lowers the brittleness of the glass. Contents which are too high, however, may result in the glass becoming highly reactive, particularly in the environment of dental polymers. The glass, in contrast, is to be at least very largely inert towards dental polymers, especially composites, and is for example not to interfere with their polymerization behaviour. In one advantageous variant, the glass is free from zirconium oxide ($ZrO_2$-free).

One advantageous embodiment of a radiopaque glass may comprise a limited proportion of alkaline earths from the CaO and MgO group. The proportion of CaO may be 0 to 2 wt %. MgO is likewise optional and may be present at from 0 to 2 wt %. In one especially preferred embodiment, the glass according to the invention is free from MgO, apart from impurities at most. MgO may be disadvantageous in glasses for dental applications, which are to combine low refractive indices with high radiopacity. MgO does not raise the radiopacity to the same extent as the other alkaline earth metal oxides CaO, SrO and BaO, because the X-ray absorption edge of MgO is well below theirs, and exhibits only a little influence in the area of the tungsten X-ray tubes used in the medical sector. MgO would merely increase the index of refraction and thereby complicate the balance between low index of refraction and high radiopacity.

The glass according to the invention can be free from $CeO_2$ and $TiO_2$, optionally, apart from impurities at most. On account of their absorption in the UV region, $CeO_2$ and $TiO_2$ shift the UV edge of the glass, which may consequently acquire an unwanted yellowish coloration. In one preferred embodiment, the glass according to the invention is $TiO_2$-free.

One particularly preferred embodiment of the glass is free from $TiO_2$ and $ZrO_2$.

ZnO and/or $WO_3$ and/or $Nb_2O_5$ and/or $HfO_2$ and/or $Ta_2O_5$ and/or $Gd_2O_3$ and/or $Sc_2O_3$ and/or $Y_2O_3$ and/or $Yb_2O_3$ may be additionally present preferably and optionally individually or in any combinations at 0 to 2 wt % in each case.

In the context of the invention, $La_2O_3$ can advantageously be used with a proportion of 0 to 19 wt %, preferably 0 to 16 wt. % or 0 to 15 wt % in order to adjust the desired radiopacity of the glasses. If $La_2O_3$ is comprised, it will advantageously be present in the glass with at least 0.1 wt %, preferably at least 0.2 wt %, preferred at least 0.5 wt % or at least 1 wt % in general. Preferably, $La_2O_3$-containing glasses comprise more than 2 wt % of this component. Some advantageous variants have a suitable lower limit of 4 wt %. An advantageous upper limit of $La_2O_3$ may be 19 wt % or 18 wt %, preferably 17 wt % or 16 wt % or 15 wt %. Other advantageous variants can have a suitable upper limit for $La_2O_3$ of 13 wt % or 11 wt % or 10 wt % or 9 wt % or 8 wt % or 7.5 wt % or 6 wt % or 5 wt %.

As an alternative for $La_2O_3$-containing variants, the invention comprises advantageous variants having a significantly reduced content of $La_2O_3$. These variants contain not more than 2 wt %, preferably not more than 1.5 wt % or not more than 1 wt % of $La_2O_3$ ($La_2O_3$-poor variants). If $La_2O_3$ shall be present in these variants, 0.1 wt % can be an advantageous lower limit for it. The restriction of the $La_2O_3$ content has the advantageous effect that the refractive index of the glass is not increased too much. One preferred embodiment of the glass is free from $La_2O_3$ ($La_2O_3$-free variant). This offers cost advantages and allows the production of low-index glasses with high radiopacity.

It is possible for the radiopaque glass, for technical or optical applications, to comprise at least one refining agent, selected for example from the group of chlorides or sulphates, with a proportion of 0 to 2 wt %, advantageously of 0 to 1 wt %. $SnO_2$ as well can be used as a refining agent, with the advantage over refining agents that are likewise possible, such as $As_2O_3$ and $Sb_2O_3$, and also the stated chlorides and sulphates, that no contamination by other refining agents is carried into the melting assemblies. This is advantageous if, subsequent to technical glasses, dental glasses are produced again.

The linear coefficient of thermal expansion $\alpha_{(20-300)}$, measured in the temperature interval from 20° C. to 300° C., of the glass according to the invention is preferably less than $7 \times 10^{-6}$ $K^{-1}$. As a result of the low coefficient of thermal expansion, the glasses according to the invention, especially when used as filling material in polymers, are capable of compensating the natural, high thermal expansion of the polymers, thus giving the polymer-based dental composition a thermal expansion which is better adapted to the natural tooth material.

As already described, the glasses according to the invention are resistant to chemical attack—that is, they are chemically stable. They preferably have a water resistance HGB in accordance with DIN ISO 719 of Class 2 or better.

The glasses according to the invention are therefore notable for good chemical resistance, resulting in a high degree of inertness in combination with the resin matrix, and thus with a very long lifetime of the dental composition as a whole.

According to a further preferred embodiment of the present invention, the glass according to the invention is also preferably free from other components not stated in the claims and/or in the present description. This means that according to one such embodiment, the glass substantially consists of the stated components. The expression "substantially consist" here means that other components are present as impurities at the most, but are not deliberately added as an individual component to the glass composition.

Nevertheless, the invention also envisages the use of the glass according to the invention as a basis for further glasses, in which up to 5 wt % of further components may be added to the glass according to the invention described. In such a case the glass consists, in accordance with the invention, of the glass described to an extent of at least 95 wt %.

It is, of course, also possible to adapt the coloured appearance of the glass for optical or other technical applications through the addition of oxides customary for the purpose. Oxides suitable for colouring glasses are known to the skilled person, examples including CuO and CoO, which for these purposes may be added preferably at from 0 to 0.5 wt %. Moreover, the glass may be given an antiseptic function through additions, for example, of $Ag_2O$ at 0 to 3 wt %.

The invention further encompasses glass powders composed of the glasses according to the invention, and the use of a radiopaque glass according to the invention as glass powder. The glass powders can be produced by known methods, as described for example in DE 41 00 604 C1. The glass powder according to the invention and/or the powder particles preferably have an average particle size of up to 50 µm, more preferably up to 20 µm. An average particle size of 0.1 µm may be reached as a lower limit, wherein of course smaller particle sizes are also encompassed by the invention. The aforementioned glass powder may serve as starting material for the use of the glasses according to the invention as fillers and/or dental glasses in general. An advantageous use of a radiopaque glass according to the invention is in a dental glass/polymer dental composition comprising dental polymer. A dental composition of this kind finds use, for example, as dental filling material, material for inlays, onlays, dental cement, facing material for crowns and bridges, material for artificial teeth, and/or other material for prosthetic, preservative and/or preventive dental treatment.

In one preferred embodiment, the surface of the glass powder, i.e. the surface of the glass powder particles, is silanized by the customary techniques. Silanization makes it possible to improve the binding of the inorganic fillers to the polymer matrix of the polymer-based dental composition.

The object stated at the outset is further achieved by a radiopaque glass according to the invention for use in the medical sector, more particularly in the dental medical sector as dental glass, and/or for diagnostic purposes. Diagnostic purposes include medical applications, an example being use in a contrast medium.

Furthermore, the object stated at the outset is achieved by a radiopaque glass according to the invention for use as dental glass for treating cavities in human and/or animal teeth and/or for dental restoration. The treatment generally comprises complete or partial filling of a cavity, a hollow, a gap, etc., in a tooth.

The glass according to the invention may be used as described preferably as dental glass. In that case it is advantageous if the dental glass is in the form of powder particles. It is further advantageous if it is a constituent of a polymer-based dental composition comprising dental polymer, more particularly forming a filler in powder form. The surfaces of the powder particles are preferably silanized. In one advantageous embodiment, further components may be admixed to the dental composition in addition to the glass powder, examples being a barium and/or strontium and/or lithium alum inate glass-ceramic powder, an addition for further increasing the radiopacity (e.g. ytterbium trifluoride and/or yttrium fluoride), or a filler for adjusting the viscosity (more particularly fumed and/or wet-precipitated silica).

The dental glass preferably finds application as a filler in composites (also called filling composites) for the treatment, more particularly the filling, of dental cavities and/or for dental restoration, more preferably for acrylate-based polymers, which require largely chemically inert fillers. Likewise within the context of the invention is the use of the glass according to the invention as a radiopacifier in dental compositions, especially polymer-based dental compositions. The glass according to the invention is a suitable replacement for expensive crystalline radiopacifiers such as $YbF_3$, for example. The glass according to the invention is also suitable and intended for use as a filler in dental cements, e.g. glass ionomer cements. It is likewise possible for the glass according to the invention to be used as an inert additive in glass ionomer cements. Particularly preferred is the use as an inert additive in polymer-reinforced glass ionomer cements. The polymer-reinforced glass ionomer cements comprise a class of materials available for the past few years, exhibiting per se the curing reaction of a cement, which may take a very long time, but also including a resin matrix like the composite described above, so as to be curable initially.

Correspondingly, the radiopaque glass according to the invention is used preferably for producing a dental glass/polymer composite comprising a dental polymer. The dental polymer preferably comprises a UV-curable resin based on acrylate, methacrylate, 2,2-bis[4-(3-methacryloyloxy-2-hydroxypropoxy)phenyl]propane (bis-GMA), triethylene glycol dimethacrylate (TEGDMA or TEGMA, depending on what is meant here), urethane dimethacrylate (UDMA), alkanediol dimethacrylate or cyanoacrylate.

Likewise encompassed by the invention is the use of the glass according to the invention as an optical element which comprises the glass according to the invention. Optical elements are understood to be all articles, and especially components, which may be employed for optical applications. These may be components through which light passes. Examples of such components are cover glasses and/or lens elements, but also supports of other components, such as mirrors and glass fibres, for example.

Cover glasses are used preferably for protecting electronic components. These, of course, likewise include optoelectronic components. The cover glasses are present customarily in the form of glass plates having plane-parallel surfaces and are preferably mounted above the electronic component, thereby protecting it from environmental effects, but allowing electromagnetic radiation such as light and X-radiation, for example, to pass through the cover glass and interact with the electronic component. For certain optoelectronic components, however, X-radiation may also be harmful. A cover glass produced from the radiopaque glass according to the invention may therefore be used for instances such as X-ray protective glass, for example, in medical apparatus.

A further possible application is the use of the radiopaque glass according to the invention as cover glass and/or substrate glass in display technology for cathode ray tubes (CRT).

On the basis of its optical properties, the glass according to the invention may likewise be used for optical applications. Being largely chemically inert, it is suitable for applications as substrate glass and/or cover glass in photovoltaics, as for example for the covering of silicon-based photovoltaic cells, of organic photovoltaic cells and/or as support material for thin-film photovoltaic modules. The X-ray absorption of the glass according to the invention has particular advantages, among others, in the use of photovoltaic modules in aerospace applications, since these modules may be exposed to particularly intense X-radiation outside the Earth's atmosphere. The property of the high X-ray absorption, moreover, allows the glass to be used, very generally, as X-ray protective glass.

By virtue of its high temperature stability, the glass according to the invention is also suitable as lamp glass, particularly for use in halogen lamps and/or fluorescent tubes and related constructions. If the mechanisms of light generation in the lamp give rise to X-radiation, a particular advantage of the glass according to the invention is that this radiation can be kept away from the surroundings. Furthermore, the glass according to the invention can be used in X-ray tubes.

Additionally encompassed by the invention is the vaporization of the glass according to the invention by physical methods and the deposition of the vaporized glass on components. Such physical vapour deposition processes, also called PVD processes for short, are familiar to the skilled person and described for example in DE 102 22 964 B4. In such processes, the glass according to the invention serves as the target to be vaporized. The components vapour-coated with the glass according to the invention may benefit both from the chemical resistance of the glass and from its X-ray absorption.

Furthermore, on account of their high stability, the glasses according to the invention are likewise suitable as matrix material for the secure temporary and/or permanent storage of radioactive waste, and also for the embedding of radioactive materials.

This glass also exhibits advantages in application as container glass or packaging for pharmaceutical products. In view of the high stability with respect to ambient media, interactions with ingredients can be almost ruled out.

EXAMPLES

The invention is illustrated below with examples which elucidate the teaching of the invention but are not intended to restrict it.

TABLE 1

Working examples (AB) in wt %

| | Example No. | | | | | | | | |
|---|---|---|---|---|---|---|---|---|---|
| | AB1 | AB2 | AB3 | AB4 | AB5 | AB6 | AB7 | AB8 | AB9 |
| $SiO_2$ | 42.7 | 63.8 | 66.2 | 61.5 | 53.8 | 54.1 | 51.3 | 48.3 | 45.3 |
| $B_2O_3$ | 8.3 | 13.8 | 11.9 | 10.5 | 10.4 | 8.9 | 9.5 | 8.3 | 7.9 |
| $Al_2O_3$ | 3.6 | 1.3 | 4.7 | 6.3 | 5.2 | 5.9 | 5.0 | 4.9 | 4.1 |
| $K_2O$ | | 2.6 | 2.7 | 3.9 | 3.6 | 3.6 | 3.2 | 3.4 | 2.4 |
| $Cs_2O$ | 16.7 | 8.5 | 3.0 | 5.8 | 9.8 | 5.4 | 9.6 | 11.8 | 15.3 |
| BaO | 18.2 | 4.7 | 2.2 | 3.1 | 8.8 | 13.7 | 13.3 | 15.5 | 15.8 |
| $SnO_2$ | 8.9 | 4.2 | 7.5 | 7.2 | 6.7 | 6.7 | 6.5 | 6.3 | 7.7 |
| $ZrO_2$ | — | — | — | — | — | — | — | — | — |
| F | 1.6 | 1.1 | 1.9 | 1.8 | 1.7 | 1.7 | 1.6 | 1.6 | 1.5 |
| $Cs_2O + BaO + SnO_2 + F$ | 45.4 | 18.5 | 14.6 | 17.9 | 27.0 | 27.5 | 31.0 | 35.2 | 40.3 |
| Total | 100.0 | 100.0 | 100.0 | 100.0 | 100.0 | 100.0 | 100.0 | 100.0 | 100.0 |
| $n_d$ | 1.548 | 1.497 | 1.488 | 1.495 | 1.515 | 1.522 | 1.525 | 1.533 | 1.543 |
| Density (g/cm³) | 3.15 | 2.49 | 2.36 | 2.46 | 2.67 | 2.71 | 2.78 | 2.90 | 3.00 |
| Rel. ALET (%) | 1240 | 420 | 310 | 410 | 670 | 690 | 800 | 940 | 1130 |
| Hydrolytic class to DIN ISO 719 | | | | | HGB1 | | HGB1 | | |
| Thermal expansion α (20-300° C.) ($10^{-6} K^{-1}$) | 5.9 | 4.3 | | | 5.3 | | 5.9 | | |

| | Example No. | | | | | |
|---|---|---|---|---|---|---|
| | AB10 | AB11 | AB12 | AB13 | AB14 | AB15 |
| $SiO_2$ | 40.6 | 68.4 | 38.8 | 52.4 | 52.0 | 49.6 |
| $B_2O_3$ | 7.4 | 12.4 | 7.3 | 9.7 | 9.5 | 9.2 |
| $Al_2O_3$ | 3.3 | 4.8 | 3.2 | 3.8 | 5.1 | 4.9 |
| $K_2O$ | 3.0 | 2.7 | 2.9 | 0.8 | 3.3 | 3.1 |
| $Cs_2O$ | 24.0 | 3.1 | 25.0 | 9.8 | 8.0 | 9.3 |
| BaO | 12.2 | 1.1 | 12.8 | 15.6 | 13.5 | 12.9 |
| $SnO_2$ | 8.0 | 6.0 | 8.6 | 6.7 | 6.6 | 6.3 |
| $ZrO_2$ | — | — | — | — | 0.8 | — |
| F | 1.4 | 1.5 | 1.4 | 1.2 | 1.2 | 4.8 |
| $Cs_2O + BaO + SnO_2 + F$ | 45.6 | 11.7 | 47.8 | 33.3 | 29.3 | 33.3 |
| Total | 100.0 | 100 | 100 | 100.0 | 100.0 | 100.0 |
| $n_d$ | 1.553 | 1.481 | 1.559 | 1.527 | 1.526 | 1.504 |
| Density (g/cm³) | 3.14 | 2.4 | 3.24 | 2.83 | 2.79 | 2.75 |
| Rel. ALET (%) | 1340 | 140 | 1395 | 830 | 783 | 775 |
| Hydrolytic class to DIN ISO 719 | | | | | | |
| Thermal expansion α (20-300° C.) ($10^{-6} K^{-1}$) | | | | | | |

Table 1 encompasses working examples of the radiopaque glass in the preferred compositional range. All data pertaining to the composition is listed in wt %. The glasses contain the advantageous radiopacifier combination of $Cs_2O$, BaO and $SnO_2$, and additionally a defined amount of fluorine. The stated combination and fluorine together form an advantageous radiopacifier system, with which the index of refraction in the range from 1.480 to 1.561 and the relative aluminium equivalent thickness in the range from approximately 120% up to more than approximately 1400% can be established.

All values for the relative aluminium equivalent thickness (ALET in %) that are listed in Table 1, corresponding to X-ray absorption (XRO in %), were determined in a method based on DIN ISO 4049. The grey values determined in the image were measured using image processing software and used for determination of the X-ray absorption. Table 1 additionally lists the refractive indices $n_d$ and densities of the working examples.

The glasses described in the examples were produced as follows:

The raw materials for the oxides are weighed out and then thoroughly mixed. The glass batch is melted at about 1580° C. in a discontinuous melting assembly, then refined and homogenized. At a casting temperature of about 1600° C., the glass can be cast and processed as ribbons or in other desired dimensions. In a high-volume, continuous assembly, the temperatures can be reduced by at least about 100 K.

For further processing, the cooled glass ribbons were milled by means of the method known from DE 41 00 604 C1 to form a glass powder having an average particle size of not more than 10 μm. The glass properties were determined on glass bulks which had not been milled into powders. The glasses have good chemical resistance with respect to water.

Additionally listed in Table 1 is the chemical resistance of variants of the glass according to the invention. Given by way of example for two examples is the hydrolytic resistance class (HGB) according to DIN ISO 719. The glasses according to the invention, however, also attain good values for acid resistance according to DIN 12116 and for alkali resistance according to DIN ISO 695.

The following table G1500 shows glasses having a refractive index in the range of 1.50. The values are given in wt %.

| | Table G 1500, example-no. | | | | | | | | |
|---|---|---|---|---|---|---|---|---|---|
| | 500-1 | 500-2 | 500-3 | 500-4 | 500-5 | 500-6 | 500-7 | 500-8 | 500-9 |
| $SiO_2$ | 54.2 | 61.2 | 57.0 | 54.8 | 61.6 | 61.4 | 60.3 | 61.5 | 60.2 |
| $B_2O_3$ | 9.5 | 13.4 | 9.2 | 9.4 | 13.5 | 13.4 | 8.9 | 13.5 | 8.9 |
| $Al_2O_3$ | 5.1 | 1.3 | 4.9 | 5.0 | 1.3 | 1.3 | 4.7 | 1.3 | 4.7 |
| $K_2O$ | 3.2 | 4.2 | 3.1 | 3.9 | 4.2 | 4.2 | 3.0 | 4.2 | 3.0 |
| $Cs_2O$ | 9.6 | 15.9 | 9.3 | 9.5 | 19.4 | 17.8 | 9.0 | 18.3 | 9.0 |
| SrO | | | | | | | | | |
| BaO | 13.4 | | 12.9 | 13.2 | | | 12.5 | | 12.3 |
| $SnO_2$ | | | | | | | | | |
| $ZrO_2$ | | | | | | | | | |
| F | 5.0 | | 3.4 | 4.3 | | | 1.6 | | 1.6 |
| $La_2O_3$ | | 4.0 | | | | 1.9 | | 1.2 | |
| $Cs_2O + BaO + SnO_2 + F$ | 28.0 | 15.9 | 25.7 | 27.0 | 19.4 | 17.8 | 23.0 | 18.3 | 22.9 |
| Total | 100 | 100 | 100 | 100 | 100 | 100 | 100 | 100 | 100 |
| $n_d$ | 1.486 | 1.505 | 1.492 | 1.490 | 1.496 | 1.502 | 1.504 | 1.501 | 1.504 |
| Density (g/cm$^3$) | 2.63 | 2.58 | 2.63 | 2.64 | 2.52 | 2.57 | 2.65 | 2.57 | 2.65 |
| Rel. ALET [%] | 543 | 478 | 531 | 577 | 462 | 474 | 517 | 473 | 517 |
| Hydrolytic Class to DIN ISO 719 | | | | | | HGB2 | HGB1 | | HGB1 |
| Thermal Expansion α (20-300° C.) (10$^{-6}$ K$^{-1}$) | 6.1 | 5.4 | 5.7 | 6.1 | 5.3 | 5.5 | 5.2 | 5.5 | 5.2 |

The following table G 1515 shows glasses having a refractive index in the range of 1.515. The values are given in wt %.

| | Table G 1515, example-no. | | | | | | | |
|---|---|---|---|---|---|---|---|---|
| | 515-10 | 515-11 | 515-12 | 515-13 | 515-14 | 515-15 | 515-16 | 515-17 |
| $SiO_2$ | 50.9 | 61.9 | 62.0 | 51.4 | 59.3 | 49.7 | 58.4 | 50.4 |
| $B_2O_3$ | 9.8 | 13.6 | 13.8 | 9.8 | 13.2 | 9.6 | 13.1 | 9.7 |
| $Al_2O_3$ | 4.9 | 1.3 | 1.3 | 4.9 | 1.3 | 4.8 | 1.3 | 4.8 |
| $K_2O$ | 3.5 | 4.3 | 4.3 | 3.4 | 4.1 | 3.3 | 4.1 | 3.3 |
| $Cs_2O$ | 21.0 | 8.4 | 8.5 | 21.0 | 11.9 | 23.3 | 13.1 | 22.3 |
| BaO | 8.3 | 4.2 | 4.2 | 8.3 | 4.1 | 8.1 | 4.0 | 8.2 |
| $SnO_2$ | | | | | | | | |
| $ZrO_2$ | | | 1.7 | | | | | |
| F | 1.6 | | | 1.3 | | 1.3 | | 1.3 |
| $La_2O_3$ | | 6.3 | 4.1 | | 6.1 | | 6.0 | |
| $Cs_2O + BaO + SnO_2 + F$ | 30.9 | 12.6 | 12.7 | 30.6 | 16.0 | 32.7 | 17.1 | 31.8 |
| Total | 100 | 100 | 100 | 100 | 100 | 100 | 100 | 100 |
| $n_d$ | 1.514 | 1.510 | 1.508 | 1.512 | 1.514 | 1.517 | 1.517 | 1.515 |
| Density (g/cm$^3$) | 2.81 | 2.58 | 2.55 | 2.77 | 2.64 | 2.85 | 2.67 | 2.83 |

-continued

| | | | | | | | | |
|---|---|---|---|---|---|---|---|---|
| Rel. ALET (%) | 938 | 446 | 437 | 725 | 530 | 792 | 560 | 766 |
| Hydrolytic Class to DIN ISO 719 | | | | | | | | |
| Thermal Expans. α (20-300° C.) ($10^{-6}$ $K^{-1}$) | 6.5 | 4.9 | 4.6 | 6.1 | 5.2 | 6.6 | 5.5 | 6.5 |

| | Table G 1515 continuation, example-no. | | | | | | | |
|---|---|---|---|---|---|---|---|---|
| | 515-18 | 515-19 | 515-20 | 515-21 | 515-22 | 515-23 | 515-24 | 515-25 |
| $SiO_2$ | 58.9 | 55.4 | 56.2 | 57.6 | 52.1 | 52.0 | 57.9 | 58.2 |
| $B_2O_3$ | 13.2 | 10.5 | 10.6 | 8.8 | 8.0 | 9.7 | 12.9 | 10.8 |
| $Al_2O_3$ | 1.3 | 3.1 | 3.1 | 3.1 | 4.9 | 4.9 | 1.2 | 3.2 |
| $K_2O$ | 4.1 | 3.7 | 3.8 | 3.8 | 3.2 | 3.5 | 4.0 | 3.8 |
| $Cs_2O$ | 12.3 | 17.4 | 17.7 | 17.7 | 23.0 | 28.4 | 17.1 | 19.8 |
| BaO | 4.1 | 6.2 | 7.4 | 7.8 | 8.3 | | | |
| $SnO_2$ | | | | | | | | |
| $ZrO_2$ | | | | | | | 0.8 | |
| F | | 0.7 | 0.7 | 0.7 | 0.8 | 1.6 | | 0.7 |
| $La_2O_3$ | 6.1 | 3.0 | 0.5 | 0.5 | | | 6.0 | 3.5 |
| $Cs_2O + BaO + SnO_2 + F$ | 16.4 | 24.3 | 25.8 | 26.2 | 32.1 | 30.0 | 17.1 | 19.8 |
| Total | 100 | 100 | 100 | 100 | 100 | 100 | 100 | 100 |
| $n_d$ | 1.516 | 1.517 | 1.515 | 1.516 | 1.519 | 1.510 | 1.515 | 1.511 |
| Density (g/cm³) | 2.66 | 2.76 | 2.75 | 2.76 | 2.87 | 2.85 | 2.68 | 2.69 |
| Rel. ALET (%) | 542 | 663 | 639 | 653 | 795 | 729 | 571 | 576 |
| Hydrolytic Class to DIN ISO 719 | HGB2 | HGB2 | | HGB2 | | | | |
| Thermal Expans. α (20-300° C.) ($10^{-6}$ $K^{-1}$) | 5.4 | 6.0 | 6.0 | 6.0 | 6.8 | 6.0 | 5.3 | 5.6 |

The following table G 1525 shows glasses having a refractive index in the range of 1.525. The values are given in wt %.

| | Table G 1525, example-no. | | | | | | |
|---|---|---|---|---|---|---|---|
| | 525-13 | 525-15 | 525-16 | 525-18 | 525-19 | 525-20 | 525-21 |
| $SiO_2$ | 53.5 | 52.2 | 52.3 | 47.9 | 58.9 | 57.7 | 57.0 |
| $B_2O_3$ | 9.9 | 9.7 | 9.8 | 9.7 | 13.4 | 13.3 | 13.1 |
| $Al_2O_3$ | 5.1 | 5.0 | 5.0 | 4.6 | 1.3 | 1.3 | 1.3 |
| $K_2O$ | 3.2 | 3.1 | 3.2 | 11.5 | 4.2 | 4.2 | 4.1 |
| $Cs_2O$ | 9.7 | 9.5 | 9.5 | 10.7 | 8.3 | 8.2 | 10.0 |
| BaO | 13.1 | 12.9 | 12.9 | | 8.2 | 9.7 | 10.6 |
| $SnO_2$ | | | | | | | |
| $ZrO_2$ | | | | | 1.7 | 1.7 | |
| F | 1.2 | 1.2 | 1.2 | | | | |
| $La_2O_3$ | 4.3 | 6.3 | 6.0 | 15.6 | 4.0 | 4.0 | 3.9 |
| $Cs_2O + BaO + SnO_2 + F$ | 24.0 | 23.6 | 23.6 | 10.7 | 16.5 | 17.9 | 20.6 |
| Total | 100 | 100 | 100 | 100 | 100 | 100 | 100 |
| $n_d$ | 1.521 | 1.526 | 1.525 | 1.539 | 1.521 | 1.525 | 1.526 |
| Density (g/cm³) | 2.79 | 2.82 | 2.82 | 2.82 | 2.67 | 2.71 | 2.74 |
| Rel. ALET (%) | 667 | 710 | 706 | 670 | 539 | 575 | 603 |
| Hydrolytic Class to DIN ISO 719 | | | HGB1-2 | | | | |
| Thermal Expans. α (20-300° C.) ($10^{-6}$ $K^{-1}$) | 5.9 | 6.0 | 6.0 | 8.0 | 5.3 | 5.4 | 5.8 |

| | Table G 1525 continuation, example-no. | | | | | | |
|---|---|---|---|---|---|---|---|
| | 525-22 | 525-23 | 525-24 | 525-26 | 525-28 | 525-27 | 525-29 |
| $SiO_2$ | 55.9 | 51.6 | 51.8 | 52.4 | 53.4 | 50.2 | 57.1 |
| $B_2O_3$ | 13.0 | 9.6 | 9.6 | 9.5 | 9.4 | 7.8 | 5.4 |
| $Al_2O_3$ | 1.3 | 5.0 | 4.9 | 4.9 | 4.8 | 4.5 | 1.4 |
| $K_2O$ | 4.1 | 3.1 | 3.1 | 3.1 | 3.0 | 2.2 | 0.2 |
| $Cs_2O$ | 15.6 | 11.2 | 11.9 | 15.4 | 15.3 | 19.6 | 14.7 |
| BaO | 9.7 | 12.5 | 12.5 | 12.4 | 12.2 | 11.9 | 19.9 |
| $SnO_2$ | 0.5 | | | | | | |
| $ZrO_2$ | | | | | | | |
| F | | 1.1 | 1.0 | 0.5 | | 0.8 | 1.1 |
| $La_2O_3$ | | 5.8 | 5.2 | 1.9 | 1.9 | 3.0 | 0.2 |
| $Cs_2O + BaO + SnO_2 + F$ | 25.8 | 24.8 | 25.4 | 28.2 | 27.5 | 32.3 | 35.7 |
| Total | 100 | 100 | 100 | 100 | 100 | 100 | 100 |
| $n_d$ | 1.522 | 1.526 | 1.526 | 1.525 | 1.525 | 1.528 | 1.528 |

-continued

| | | | | | | | |
|---|---|---|---|---|---|---|---|
| Density (g/cm³) | 2.74 | 2.84 | 2.84 | 2.84 | 2.85 | 2.94 | 2.95 |
| Rel. ALET (%) | 647 | 738 | 740 | 747 | 744 | 906 | 888 |
| Hydrolytic Class to DIN ISO 719 | | | | HGB2 | | HGB1 | |
| Thermal Expans. α (20-300° C.) ($10^{-6}$ K$^{-1}$) | 5.9 | 6.1 | 6.1 | 6.2 | 6.2 | 6.6 | 6.0 |

| | Table G 1525 continuation example-no. | | |
|---|---|---|---|
| | 525-30 | 525-31 | 525-32 |
| $SiO_2$ | 57.4 | 57.4 | 55.0 |
| $B_2O_3$ | 12.9 | 13.0 | 8.5 |
| $Al_2O_3$ | 1.2 | 1.3 | 4.9 |
| $K_2O$ | 4.0 | 4.1 | 2.4 |
| $Cs_2O$ | 16.7 | 22.2 | 21.4 |
| MgO | | | 1.9 |
| CaO | | | 1.9 |
| BaO | | | |
| $SnO_2$ | | 0.5 | |
| $ZrO_2$ | 1.8 | 1.9 | |
| F | | | 0.9 |
| $La_2O_3$ | 6.0 | | 3.3 |
| $Cs_2O + BaO + SnO_2 + F$ | 16.7 | 22.7 | 22.3 |
| Total | 100 | 100 | 100 |
| $n_d$ | 1.520 | 1.521 | 1.525 |
| Density (g/cm³) | 2.68 | 2.74 | 2.93 |
| Rel. ALET (%) | 590 | 630 | 700 |
| Hydrolytic Class to DIN ISO719 | | | |
| Thermal Expans. α (20-300° C.) ($10^{-6}$ K$^{-1}$) | 5.5 | 5.8 | 6.5 |

The following table G 1550 shows glasses having a refractive index in the range of 1.550. The values are given in wt %.

| | Table G 1550, example-no. | | | | | | | |
|---|---|---|---|---|---|---|---|---|
| | 550-29 | 550-30 | 550-31 | 550-32 | 550-33 | 550-34 | 550-35 | 550-36 |
| $SiO_2$ | 44.1 | 42.8 | 48.1 | 45.9 | 45.1 | 46.4 | 47.0 | 50.0 |
| $B_2O_3$ | 8.1 | 9.3 | 11.6 | 7.8 | 8.1 | 7.9 | 8.1 | 4.9 |
| $Al_2O_3$ | 3.6 | 4.4 | 1.1 | 3.4 | 3.5 | 3.5 | 3.5 | 3.6 |
| $K_2O$ | | 11.0 | 3.6 | 0.5 | | | | |
| $Cs_2O$ | 16.5 | 13.4 | 13.7 | 15.7 | 16.3 | 16.1 | 16.3 | 16.4 |
| BaO | 17.9 | 7.0 | 7.1 | 17.1 | 17.7 | 17.5 | 19.0 | 19.1 |
| $SnO_2$ | | 0.9 | | 1.5 | | | | |
| F | 1.6 | | | | 1.1 | 0.5 | 0.5 | 0.5 |
| $La_2O_3$ | 8.3 | 11.2 | 14.8 | 7.9 | 8.2 | 8.1 | 5.6 | 5.6 |
| $Cs_2O + BaO + SnO_2 + F$ | 35.9 | 21.3 | 20.8 | 34.4 | 35.1 | 34.1 | 35.8 | 36.0 |
| Total | 100 | 100 | 100 | 100 | 100 | 100 | 100 | 100 |
| $n_d$ | 1.546 | 1.550 | 1.553 | 1.557 | 1.551 | 1.553 | 1.549 | 1.547 |
| Density (g/cm³) | 3.16 | 2.97 | 3.00 | 3.14 | 3.15 | 3.13 | 3.11 | 3.10 |
| Rel. ALET (%) | 1138 | 885 | 921 | 1169 | 1124 | 1105 | 1081 | 1085 |
| Hydrolytic Class to DIN ISO 719 | | | | | | | | HGB1 |
| Thermal Expansion α (20-300° C.) ($10^{-6}$ K$^{-1}$) | 6.6 | 8.4 | 6.5 | 6.4 | 6.4 | 6.3 | 6.4 | 6.3 |

| | Table G 1550 continuation, example-no. | | |
|---|---|---|---|
| | 550-37 | 550-38 | 550-39 |
| $SiO_2$ | 45.8 | 50.5 | 51.9 |
| $B_2O_3$ | 7.7 | 12.2 | 8.7 |
| $Al_2O_3$ | 3.4 | 1.2 | 3.8 |
| $K_2O$ | 0.5 | 3.8 | |
| $Cs_2O$ | 15.7 | 14.4 | 21.9 |
| MgO | | 1.0 | 1.8 |
| CaO | | 1.4 | 1.8 |
| BaO | 17.1 | | |
| $SnO_2$ | 1.5 | | |
| F | 0.3 | | 0.8 |

-continued

|  | | | |
|---|---|---|---|
| $La_2O_3$ | 7.9 | 15.5 | 9.3 |
| $Cs_2O + BaO + SnO_2 + F$ | 34.6 | 14.4 | 22.7 |
| Total | 100 | 100 | 100 |
| $n_d$ | 1.552 | 1.553 | 1.541 |
| Density (g/cm$^3$) | 3.18 | 2.96 | 3.06 |
| Rel. ALET (%) | 1180 | 783 | 850 |
| Hydrolytic Class to DIN ISO719 | | | |
| Thermal Expansion $\alpha$ (20-300° C.) ($10^{-6}$ K$^{-1}$) | 6.6 | 6.6 | 6.2 |

The glasses shown in the tables G 1500, G 1515, G 1525 and G 1550 have been experimentally melted and are thus completely or at least partially subject matter of the invention. Accordingly, the corresponding examples are also working examples.

TABLE 2

Comparative examples (VB) in wt %

| | DE102011084501 B3 | | | | | DE 102009008951A1 | | | DE 102005051387B3 | | |
|---|---|---|---|---|---|---|---|---|---|---|---|
| | | | | | | Example No. | | | | | |
| wt % | VB1 | VB2 | VB3 | VB4 | VB5 | VB6 | VB7 | VB8 | VB9 | VB10 | VB11 |
| $SiO_2$ | 59.66 | 61.14 | 59.91 | 63.28 | 64.00 | 56.26 | 52.69 | 52.09 | 58.00 | 63.00 | 58.00 |
| $B_2O_3$ | | | | 2.97 | 2.98 | 11.13 | 10.42 | 10.30 | 2.00 | 0.10 | 10.00 |
| $Al_2O_3$ | 0.86 | 0.88 | 0.89 | 1.58 | 2.28 | 5.40 | 5.06 | 5.00 | 14.00 | 12.40 | 14.00 |
| $Li_2O$ | | | 0.4 | | | | | | | | |
| $Na_2O$ | 2.41 | 2.47 | 2.48 | 1.26 | 1.26 | 2.70 | 2.53 | 0.65 | | | |
| $K_2O$ | 2.88 | 4.2 | 3.85 | 2.11 | 2.12 | 14.02 | 13.13 | 12.98 | | | |
| $Cs_2O$ | 10.95 | 7.48 | 7.53 | 11.43 | 10.69 | 4.09 | 5.31 | 8.41 | | | |
| CaO | | | 0.97 | 2.88 | 2.13 | | | | 2.00 | | |
| MgO | | | | | | | | | 7.93 | 10.40 | 6.10 |
| SrO | 11.89 | 12.19 | 12.26 | 6.81 | 6.83 | | | | | | |
| ZnO | | | | | | | | | 2.50 | | |
| $La_2O_3$ | 4.22 | 4.33 | 4.35 | 4.40 | 4.42 | | 8.59 | 4.38 | 1.57 | 8.20 | 1.50 |
| $ZrO_2$ | 7.13 | 7.31 | 7.36 | 3.28 | 3.29 | 6.42 | 2.27 | 4.82 | 2.00 | 3.90 | 0.40 |
| $WO_3$ | | | | | | | | | 10.00 | 2.00 | 10.00 |
| $SnO_2$ | | | | | | | | 1.38 | | | |
| $P_2O_5$ | | | | | | | | | | | |
| F | | | | | | | | | | | |
| Total | 100.00 | 100.00 | 100.00 | 100.00 | 100.00 | 100.00 | 100.00 | 100.00 | 100.00 | 100.00 | 100.00 |
| $n_d$ | 1.548 | 1.555 | 1.538 | 1.532 | 1.530 | 1.522 | 1.530 | 1.526 | 1.534 | 1.548 | 1.512 |
| relative ALET (%) | 763 | 679 | 684 | 638 | 617 | 276 | 395 | 472 | 352 | 276 | 263 |

| | DE19849388C2 | | U.S Pat. No. 5,641,347 | |
|---|---|---|---|---|
| | | Example No. | | |
| wt % | VB12 | VB13 | VB14 | VB15 |
| $SiO_2$ | 38 | 23 | 64.0 | 70.0 |
| $B_2O_3$ | 10 | 10 | | |
| $Al_2O_3$ | 12 | 12 | | |
| $Li_2O$ | | | | |
| $Na_2O$ | 2 | 7 | 20.0 | 25.0 |
| $K_2O$ | | | | |
| $Cs_2O$ | | | | |
| CaO | | | | |
| MgO | | | | |
| SrO | | 10 | | |
| ZnO | 6 | 6 | | |
| $La_2O_3$ | 4 | 4 | | |
| $ZrO_2$ | 3 | 3 | 16.0 | 5.0 |
| $WO_3$ | | | | |
| $SnO_2$ | | | | |

TABLE 2-continued

| Comparative examples (VB) in wt % | | | | |
|---|---|---|---|---|
| $P_2O_5$ | 5 | 10 | | |
| F | 20 | 15 | | |
| Total | 100 | 100 | 100.0 | 100.0 |
| $n_d$ | 1.514 | 1.535 | 1.548 | 1.513 |
| relative ALET (%) | 315 | 365 | 190 | 125 |

TABLE 3

| Comparative examples (VB) in mol % | | | | |
|---|---|---|---|---|
| Example No. | | EP 1 547 572 A1 | | |
| mol % | VB16 | VB17 | VB18 | VB19 |
| $SiO_2$ | 75 | 74 | 80 | 85 |
| $Li_2O$ | | | | |
| $Na_2O$ | 11 | 16 | 12 | 12 |
| $K_2O$ | | | 4 | |
| $Al_2O_3$ | | | | |
| $B_2O_3$ | | 4 | | |
| MgO | | | | |
| SrO | | | | |
| $La_2O_3$ | | | | |
| $Y_2O_3$ | 10 | | | |
| $ZrO_2$ | | 10 | 4 | 3 |
| $TiO_2$ | | | | |
| Total | 100 | 100 | 100 | 100 |
| $n_d$ | 1.52 | 1.54 | 1.50 | 1.49 |
| relative ALET [%] | 200 | 120 | 190 | 80 |

Tables 2 and 3 list, for comparison, the compositions, refractive indices and the relative aluminium equivalent thicknesses in % (i.e. the X-ray absorption, XRO, in %) of comparative examples. The glasses are known dental glasses and radiopaque glasses and/or fillers for use in dental compositions, in which the radiopacity derives in each case from various radiopacifier systems (use of individual radiopacifiers and/or a combination of different radiopacifiers).

BRIEF DESCRIPTION OF THE DRAWINGS

The figures show:

FIG. 1 shows in graph form the advantageous correlation between refractive index and relative aluminium equivalent thickness for the working examples AB1 to AB12:

It is advantageous if, within the claimed refractive index range from 1.480 to 1.561, the refractive index is assigned a relative aluminium equivalent thickness ALET (in %), as may be described by the following function:

$$\text{Relative ALET (\%)} = (15480 \text{ to } 15900) * n_d - (23015 \text{ to } 22695).$$

According to a first advantageous variant of the invention, it is advantageous if the radiopaque glass has a refractive index $n_d$ in the refractive index range between 1.480 and 1.561 and has a relative aluminium equivalent thickness ALET (%) which is greater than or equal to a minimum relative aluminium equivalent thickness (min. relative ALET) which is defined by the following equation:

$$\text{min. relative ALET (\%)} = C * n_d - D, \text{ where } C = 11000 \text{ and } D = 16160.$$

It is further advantageous if the radiopaque glass has a refractive index $n_d$ in the refractive index range between 1.480 and 1.561 and has a relative aluminium equivalent thickness ALET (%) which is less than or equal to a maximum relative aluminium equivalent thickness (max. relative ALET) which is determined by the equation:

$$\text{max. relative ALET (\%)} = A * n_d - B, \text{ where } A = 11430 \text{ and } B = 16230.$$

For the radiopaque glasses, therefore, advantageously, every refractive index in the $n_d$ range 1.480 to 1.561 may be assigned an interval of the relative ALET which is bounded by a maximum relative ALET and a minimum relative ALET. A preferred radiopaque glass having a defined refractive index $n_d$ has a relative ALET which lies advantageously in the interval of the relative ALET, the interval being calculable by the equations stated above.

Figure 2:
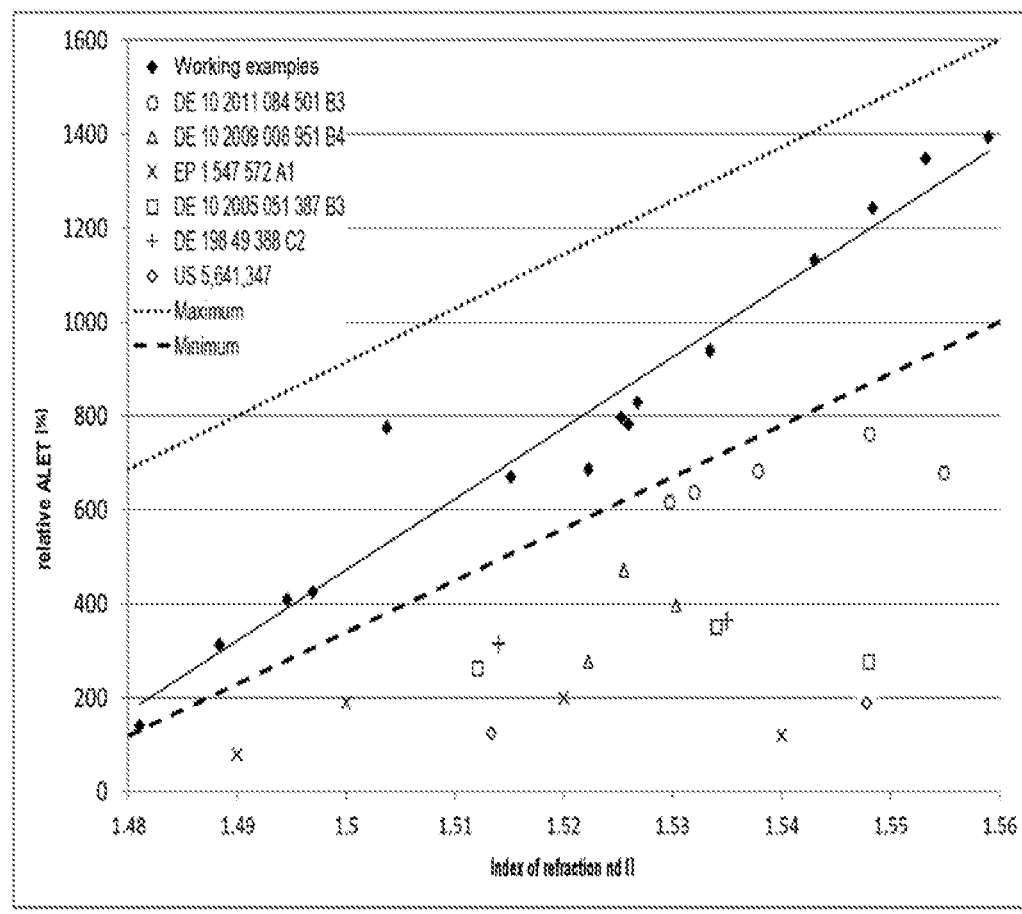
Figure 3:
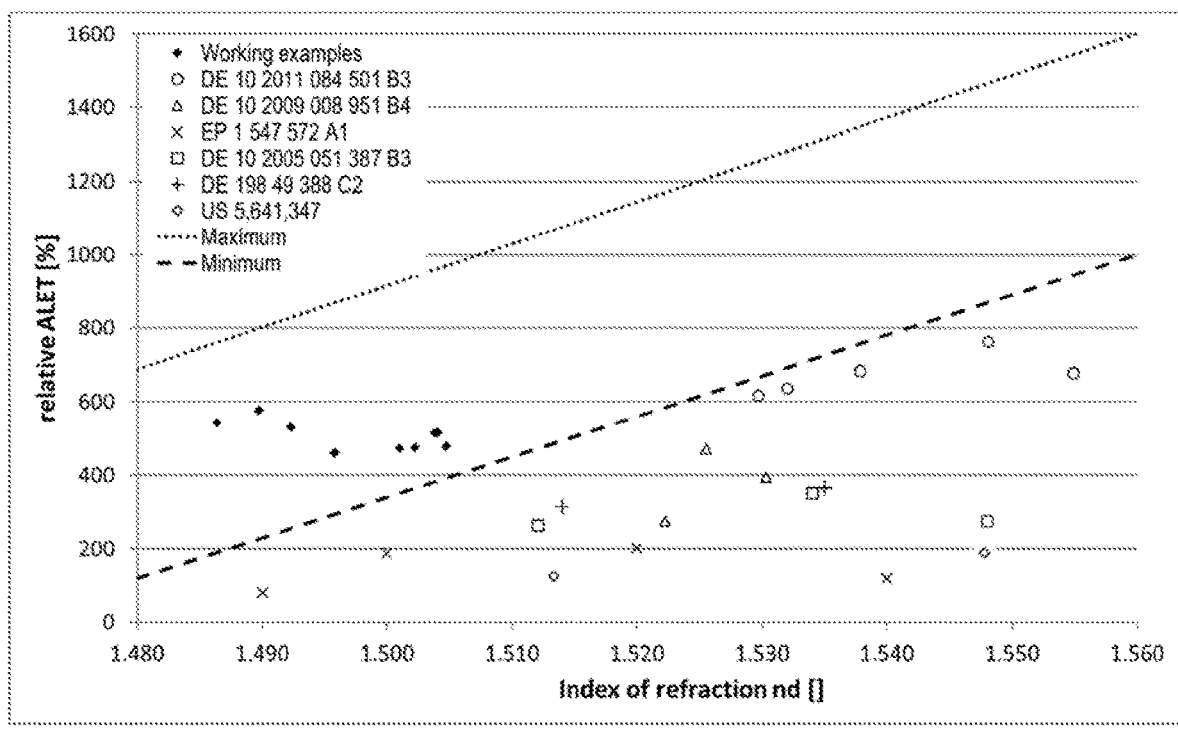
Figure 4:
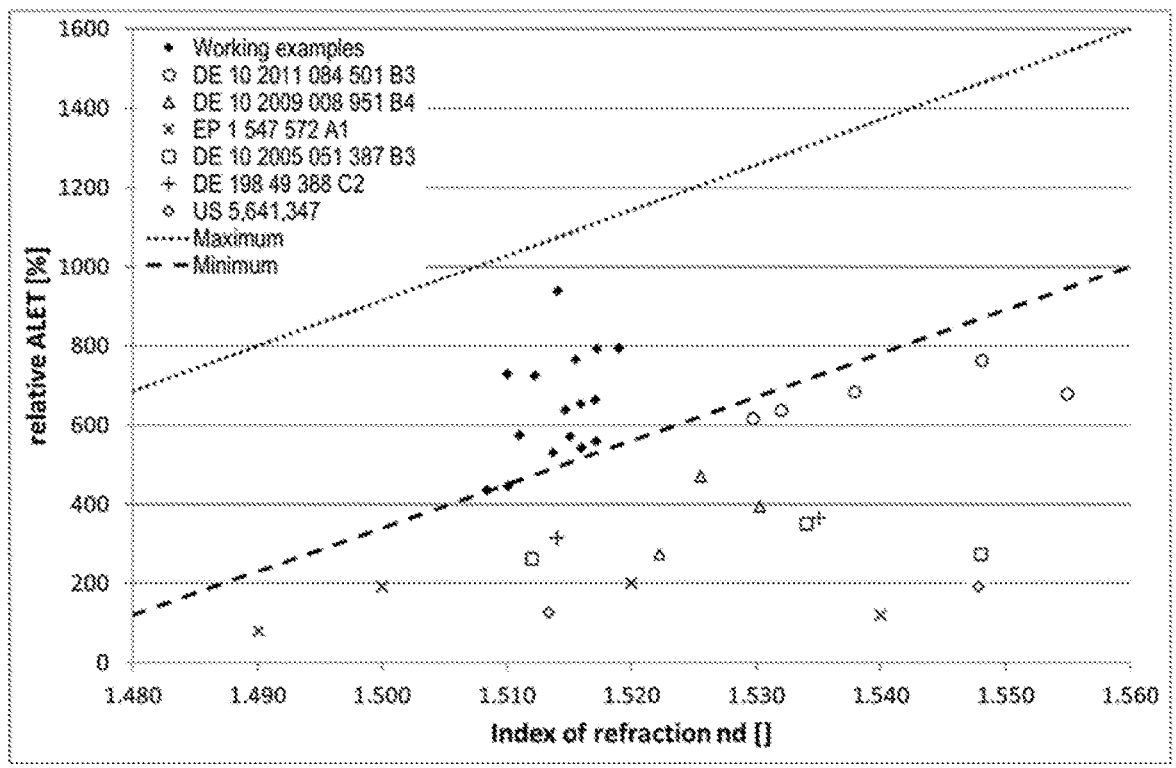
Figure 5:
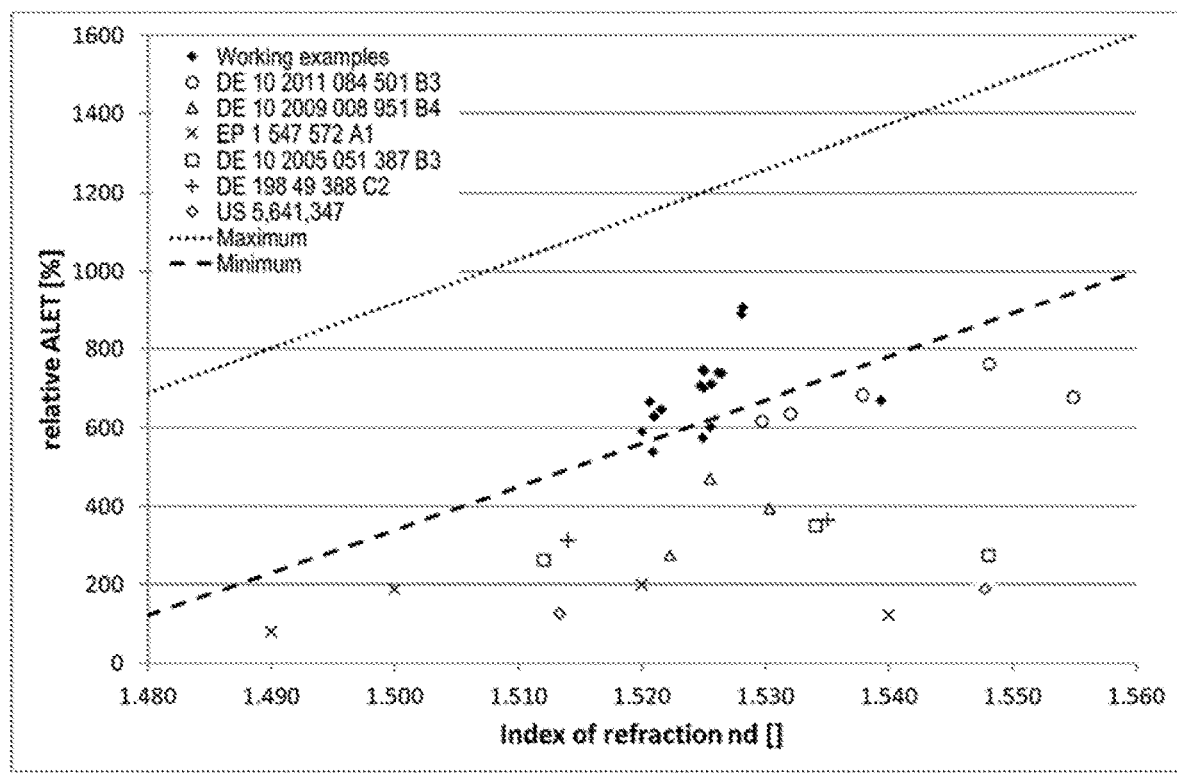
Figure 6:
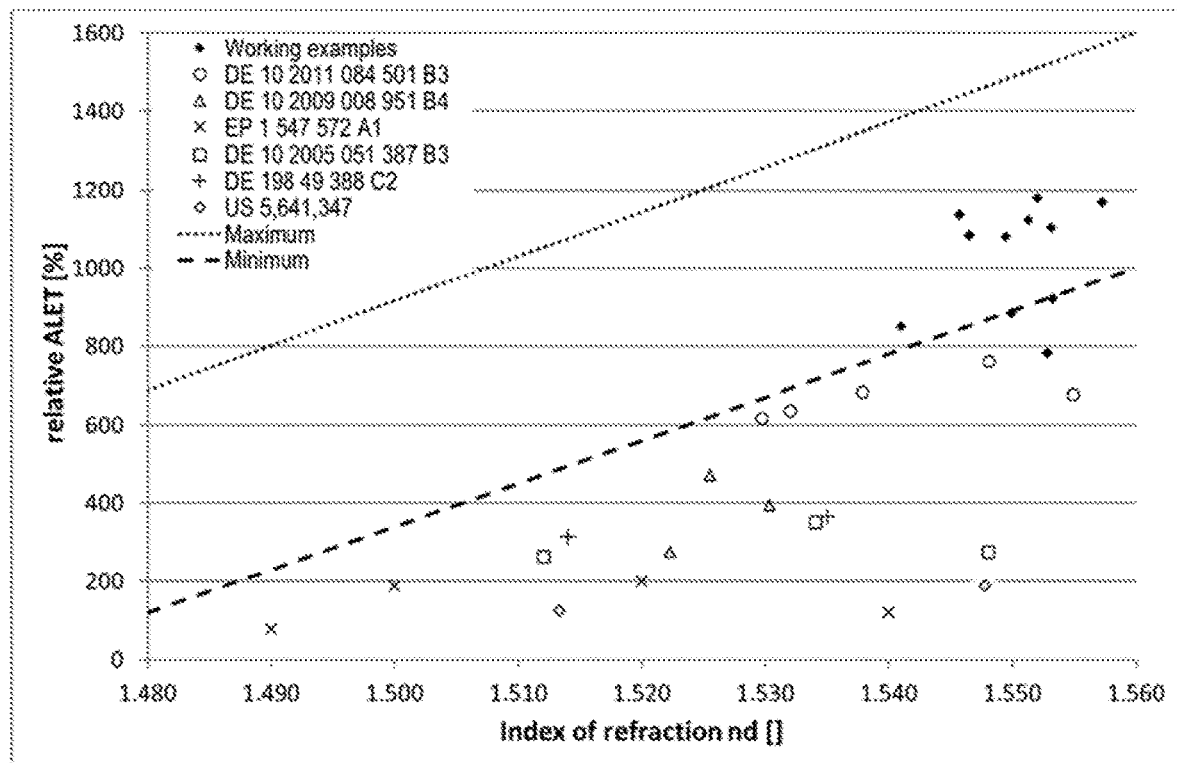

According to this first advantageous variant, the assignment ($n_d$; relative ALET) is made by the establishing of two linear equations which define the advantageous upper and lower limits of the relative ALET in the $n_d$ range from 1.480 to 1.561 for preferred variants of glasses. FIG. 2 shows the graphs of the linear equations for AB1 to AB15. The graphs form what are called "enveloping lines".

In the region between the upper enveloping line (maximum) and the lower enveloping line (minimum), the advantageous range of the relative ALET, which is assigned to the $n_d$ range from 1.480 to 1.561, is located for preferred variants of the glasses. As can be seen, the working examples are located between the "enveloping lines".

According to a second advantageous variant of the invention, in the refractive index range between 1.480 and 1.561, the assignment between the refractive index $n_d$ of the glass and the relative aluminium equivalent thickness ALET (%) is made via the statement of the following intervals:

| $n_d$ | ALET min. | and preferably | ALET max. |
|---|---|---|---|
| 1.480 to <1.490 | 120% | and preferably | 700% |
| 1.490 to <1.510 | 260% | and preferably | 1000% |
| 1.510 to <1.530 | 520% | and preferably | 1200% |
| 1.530 to <1.550 | 780% | and preferably | 1500% |
| 1.550 to 1.561 | 850%, preferably 910% | and preferably | 1600% |

What this means, to give an example, is as follows: a radiopaque glass having a given composition in accordance with the invention and a refractive index which is within the $n_d$ range between 1.490 to <1.510 (e.g. $n_d$=1.50) advantageously has a relative ALET which is at least 260% (corresponding to ALET min.). At maximum, the ALET of this glass may be preferably 1000% (corresponding to ALET max.). For radiopaque glasses which fall within other $n_d$ ranges, the other values indicated in each case for "ALET min." and "ALET max." are valid. "ALET min." therefore defines a lower limit, and "ALET max." an upper limit, for the relative ALET, referred to a defined $n_d$ range.

According to an alternative advantageous variant, in the refractive index range between 1.480 and 1.561, the assignment between the refractive index $n_d$ of the glass and the relative aluminium equivalent thickness ALET (%) is made via the statement of the following intervals:

| $n_d$ | ALET min. | and preferably | ALET max. |
|---|---|---|---|
| 1.480 to <1.490 | 120% | and preferably | 760% |
| 1.490 to <1.500 | 240% | and preferably | 875% |
| 1.500 to <1.510 | 360% | and preferably | 990% |
| 1.510 to <1.520 | 475% | and preferably | 1105% |
| 1.520 to <1.530 | 590% | and preferably | 1220% |
| 1.530 to <1.540 | 705% | and preferably | 1335% |
| 1.540 to <1.550 | 820% | and preferably | 1450% |
| 1.550 to 1.561 | 935% | and preferably | 1565% |

What this means, to give an example, is as follows: a radiopaque glass having a given composition in accordance with the invention and a refractive index which is within the $n_d$ range between 1.480 to <1.490 (e.g. $n_d$=1.485) advantageously has a relative ALET which is at least 120% (corresponding to ALET min.). At maximum, the ALET of this glass may be preferably 760% (corresponding to ALET max.). For radiopaque glasses which fall within other $n_d$ ranges, the other values indicated in each case for "ALET min." and "ALET max." are valid. "ALET min." therefore defines a lower limit, and "ALET max." an upper limit, for the relative ALET, referred to a defined $n_d$ range.

For gathering the data, glass bulks were produced from the glass compositions of the working examples, and the associated parameters were ascertained: the relative aluminium equivalent thickness (in %) was determined by the technique described above. The refractive index $n_d$ was determined in a known way. The number of samples per working example was 2. Each parameter was measured multiply, and the average values were calculated for the refractive index and the X-ray absorption. Linear regression allows the correlation between index of refraction and radiopacity to be represented for the radiopaque glasses according to the invention, e.g. for those glasses having the advantageous radiopacifier system of $SnO_2$, BaO, $Cs_2O$ and F, as shown in FIG. 1.

Figure 1:
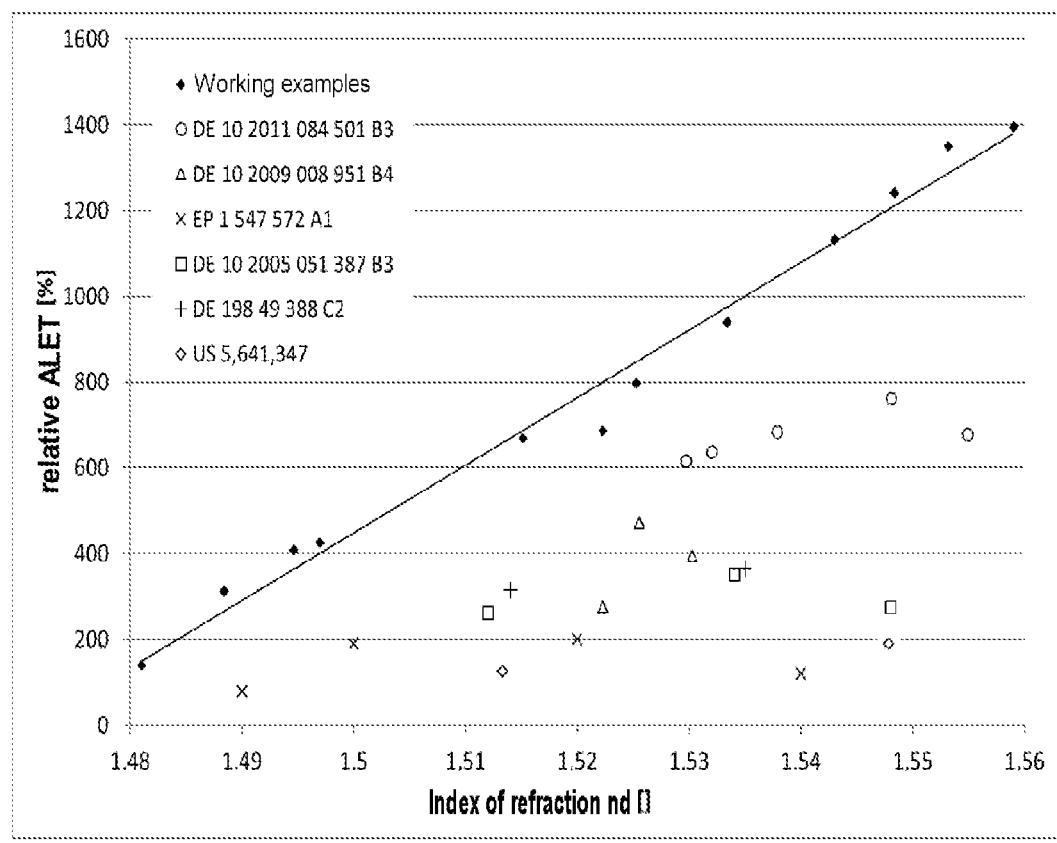
FIG. 1 the correlation between refractive index and relative aluminium equivalent thickness for the working examples of table 1, FIG. 2 the correlation between refractive index and relative aluminium equivalent thickness for the working examples of table 1 with advantageous upper and lower limits, FIG. 3 the correlation between refractive index and relative aluminium equivalent thickness for the working examples of table G 1500 with advantageous upper and lower limits, FIG. 4 the correlation between refractive index and relative aluminium equivalent thickness for the working examples of table G 1515 with advantageous upper and lower limits, FIG. 5 the correlation between refractive index and relative aluminium equivalent thickness for the working examples of table G 1525 with advantageous upper and lower limits and FIG. 6 the correlation between refractive index and relative aluminium equivalent thickness for the working examples of table G 1550 with advantageous upper and lower limits.

For comparison, index of refraction and relative aluminium equivalent thickness are likewise plotted in FIG. 1 for the stated comparative examples, which are based on different radiopacifier systems. It can be seen that the working examples in the claimed refractive index range have a much higher X-ray absorption than the comparative examples (based on the respective refractive index). For the same index of refraction, X-ray absorption values achieved in the preferred glasses are substantially higher—for example, at $n_d$=1.548, working example AB1 has a relative ALET of 1240%, while comparative example VB1 has only 763%, comparative example VB10 only 276%, and comparative example VB14 only 190%. In the low index of refraction range as well, at around 1.49, working example AB3 exhibits a relative ALET of 310%, whereas that of comparative example VB19 is only 80%. Accordingly, the X-ray visibility of the glasses preferred in the context of the invention, and of a polymer-based dental composition produced using them, is significantly increased. Accordingly, for the same thickness, optical elements (e.g. glass protective elements, etc.), comprising the preferred glass absorb more X-radiation as known optical elements or else, for the same X-ray absorption, can be made thinner, thereby allowing a weight saving to be made.

Especially in the case of glasses with low indices of refraction, it was hitherto difficult to raise the radiopacity, and possible only to raise it insufficiently, because increasing the proportion of radiopacifiers would have increased the index of refraction at the same time. With the advantageous radiopacifier system, comprising $SnO_2$, BaO, $Cs_2O$ and F, a significant rise in the radiopacity is achieved even at low indices of refraction, and, in the higher index of refraction range, the aluminium equivalent thickness is improved very greatly relative to the known glasses.

In FIG. 2, working example AB15, in relation to the radiopacifier components $Cs_2O$, BaO and $SnO_2$, exhibits a similar composition and a similarly high relative ALET as working example AB7, but with a refractive index of 1.504 has a much lower refractive index than working example AB7 ($n_d$=1.525). This is attributable to the advantageous influence of the fluorine component, allowing the refractive index to be adjusted specifically—and in this particular case, to be lowered. As a result it is possible specifically to produce a glass having a high relative ALET and a comparatively low refractive index.

A comparison of working examples AB13 and AB14, which are likewise shown in FIG. 2, makes it clear that through appropriate choice of the radiopacifiers in the preferred radiopacifier system, comprising $SnO_2$, BaO, $Cs_2O$ and F, it is possible to produce glasses having approximately the same refractive index but having different relative ALETs.

The advantageous equations, graphs and intervals described above for correlating the refractive index of a glass and the relative aluminium equivalent thickness are correspondingly valid for the working examples of the invention which are mentioned in the tables G 1500, G 1515, G 1525 and G 1550 (see FIGS. 3 to 6). In these figures the advantageous upper and lower limits ("enveloping lines") are indicated as well as comparative examples for comparison.

The invention may be additionally described by the following declarations as well:
1. Dental composition or dental material, comprising a radiopaque glass according to the invention as filler, for the treatment, more particularly for the filling, of cavities in human and/or animal teeth and/or for dental restoration.
2. Glass powder comprising powder particles composed of the radiopaque glass according to the invention.
3. Glass powder according to declaration 2, wherein the surfaces of the powder particles present are silanized.
4. Filler for polymer-based dental compositions for the treatment, more particularly filling, of cavities in human and/or animal teeth and/or for dental restoration, comprising the glass according to the invention.
5. Polymer-based dental composition comprising the radiopaque glass according to the invention or a glass powder composed of the glass according to the invention.
6. Dental glass/polymer composite comprising the radiopaque glass according to the invention or a glass powder composed of the glass according to the invention.
7. Dental glass/polymer composite according to declaration 6, wherein the dental polymer is preferably a UV-curable resin based on acrylate, methacrylate, 2,2-bis[4-(3-methacryloyloxy-2-hydroxypropoxy)phenyl]propane (bis-GMA), triethylene glycol dimethacrylate (TEGDMA or TEGMA, depending on what is meant here), urethane dimethacrylate (UDMA), alkanediol dimethacrylate or cyanoacrylate.
8. Dental glass/polymer glass ionomer cement comprising the radiopaque glass according to the invention or a glass powder composed of the glass according to the invention.
9. Use of a radiopaque glass according to the invention as dental glass for producing a dental glass/polymer dental composition comprising dental polymer for the treatment, more particularly filling, of cavities in human and/or animal teeth and/or for dental restoration.
10. Use of a radiopaque glass according to the invention as glass powder.
11. Use according to declaration 10, wherein the surfaces of the powder particles present are silanized.
12. Use according to declaration 10 or 11 in a dental glass/polymer dental composition comprising dental polymer.
13. Use of a radiopaque glass according to the invention as radiopacifier in a polymer-based dental composition and/or as
   element for optical applications and/or as
   cover glass and/or substrate glass in display technology for cathode ray tubes (CRT) and/or as
   cover glass and/or substrate glass in photovoltaics and/or as
   lamp glass in X-ray tubes and/or as
   material for the embedding of radioactive materials.
14. Radiopaque glass, being free from PbO apart from impurities at most, wherein the glass has a refractive index $n_d$ in the refractive index range between 1.480 and 1.561 and has a relative aluminium equivalent thickness ALET (%) which is greater than or equal to a minimum relative aluminium equivalent thickness (min. relative ALET) which is determined by the following equation:

min. relative ALET (%) = $C*n_d - D$, where $C=11000$ and $D=16160$.

15. Radiopaque glass, being free from PbO apart from impurities at most, wherein the glass has a refractive index $n_d$ in the refractive index range between 1.480 and 1.561 and has a relative aluminium equivalent thickness ALET (%), wherein assignment between the refractive index $n_d$ of the glass and the relative aluminium equivalent thickness ALET (%) is as follows:

| $n_d$ | ALET min. | ALET max. |
|---|---|---|
| 1.480 to <1.490 | 120% | 700% |
| 1.490 to <1.510 | 260% | 1000% |
| 1.510 to <1.530 | 520% | 1200% |
| 1.530 to <1.550 | 780% | 1500% |
| 1.550 to 1.561 | 850% | 1600% |

16. Radiopaque glass having a refractive index $n_d$ of 1.480 to 1.561, being free from PbO apart from impurities at most, comprising (in wt % based on oxide)

| | |
|---|---|
| $SiO_2$ | 35-75 |
| $B_2O_3$ | 2-16 |
| $Al_2O_3$ | 0.8-7.5 |
| $K_2O$ | 0-14 |
| BaO | 0-24 |
| $Cs_2O$ | 1-30 |
| $SnO_2$ | 0-15 |
| F | 0-8 |
| BaO + $Cs_2O$ + $SnO_2$ + F | ≥10, | and preferably comprising $La_2O_3$ with a content of 0-19

17. Radiopaque glass having a refractive index $n_d$ of 1.480 to 1.510, being free from PbO apart from impurities at most, comprising (in wt % based on oxide)

| | |
|---|---|
| $SiO_2$ | 40-70, in particular 50-65 |
| $B_2O_3$ | 5-15, in particular 6-15 |
| $Al_2O_3$ | 0.8-7.5, in particular 0.8-6 |
| $K_2O$ | 0-10, in particular 2-6 |
| BaO | 0-24, in particular 0-17 |
| $Cs_2O$ | 1-30, in particular 7-24 |
| $SnO_2$ | 0-15, in particular 0-3 |
| F | 0-8, in particular 0-6 |
| $La_2O_3$ | 0-8, in particular 0-5 |
| BaO + $Cs_2O$ + $SnO_2$ + F | ≥10, in particular 13-35 |

18. Radiopaque glass having a refractive index $n_d$ of 1.505 to 1.520, being free from PbO apart from impurities at most, comprising (in wt % based on oxide)

| | |
|---|---|
| $SiO_2$ | 42-65, in particular 47-64 |
| $B_2O_3$ | 5-15, in particular 6-15 |
| $Al_2O_3$ | 0.8-7.5, in particular 0.8-6 |
| $K_2O$ | 0-10, in particular 2-6 |
| BaO | 0-15, in particular 2-10 |
| $Cs_2O$ | 5-30, in particular 6-26 |
| $SnO_2$ | 0-10, in particular 0-3 |
| F | 0-5, in particular 0-3 |
| $La_2O_3$ | 0-9, in particular 0-7, 5 |
| BaO + $Cs_2O$ + $SnO_2$ + F | ≥9, in particular 11-35 |

19. Radiopaque glass having a refractive index $n_d$ of 1.519 to 1.542, being free from PbO apart from impurities at most, comprising (in wt % based on oxide)

| | |
|---|---|
| $SiO_2$ | 42-65, in particular 45-61 |
| $B_2O_3$ | 5-15, in particular 7-15 |
| $Al_2O_3$ | 0.8-7.5, in particular 0.8-6 |
| $K_2O$ | 0-14, in particular 1.5-7 |
| BaO | 0-18, in particular 6-14 |
| $Cs_2O$ | 5-25, in particular 6-19 |
| $SnO_2$ | 0-6, in particular 0-3 |
| F | 0-5, in particular 0-3 |
| $La_2O_3$ | 0-19, in particular 0-17 |
| BaO + $Cs_2O$ + $SnO_2$ + F | ≥8, in particular 10-35 |

20. Radiopaque glass having a refractive index $n_d$ of 1.542 to 1.561, being free from PbO apart from impurities at most, comprising (in wt % based on oxide)

| | |
|---|---|
| $SiO_2$ | 37-56, in particular 40-53 |
| $B_2O_3$ | 2-16, in particular 3-14 |
| $Al_2O_3$ | 0.8-7.5, in particular 0.8-6 |
| $K_2O$ | 0-14, in particular 0-12 |
| BaO | 0-24, in particular 4-24, preferably 4-21 |
| $Cs_2O$ | 9-25, in particular 10-19 |
| $SnO_2$ | 0-6, in particular 0-3 |
| F | 0-5, in particular 0-3 |
| $La_2O_3$ | 1-19, in particular 4-17 |
| $BaO + Cs_2O + SnO_2 + F$ | ≥10, in particular 15-42 |

21. Radiopaque glass having a refractive index $n_d$ of 1.480 to 1.561, being free from PbO and BaO apart from impurities at most, comprising (in wt % based on oxide)

| | |
|---|---|
| $SiO_2$ | 35-75, in particular 38-70 |
| $B_2O_3$ | 2-16, in particular 5-15, preferred 6-15 |
| $Al_2O_3$ | 0.8-7.5, in particular 0.8-6 |
| $K_2O$ | 0-14, in particular 0-10, preferred 0-7 |
| $Cs_2O$ | 1-30, in particular 6-28, preferred 7-24 |
| $SnO_2$ | 0-15, in particular 0-6, preferred 0-3 |
| F | 0-8, in particular 0-6, preferred 0-3 |
| $La_2O_3$ | 0-19, in particular 0-16 |
| $BaO + Cs_2O + SnO_2 + F$ | ≥10. |

With the described radiopacifier combination ($SnO_2$, BaO, $Cs_2O$) and advantageously with the defined addition of fluorine it is possible to formulate a glass having on the one hand a desired index of refraction and on the other hand an extremely high X-ray absorption. In accordance with the invention, in the refractive index range from 1.480 to 1.561, it is possible to realize a range of the relative aluminium equivalent thickness from about 120% up to more than 1400%, e.g. up to 1600%.

The examples also demonstrate that the refractive indices $n_d$ of the glass system according to the invention, particularly in a range from 1.480 to 1.561, can be adapted to the intended application without detriment to the necessary ALETs. As a result, the system can be used advantageously in particular as a filler in dental compositions, but also for other applications which impose high requirements on factors including the purity and/or the chemical resistance and temperature stability. The glass system can be produced at favourable cost on an industrial scale.

The glass according to the invention, furthermore, is relatively easy to melt and therefore efficient to produce. Found in particular has been a glass system in which, through changes in the individual constituents within the stated limits, it is possible to adjust the refractive index in line with the requirements of the application—for example, requirements asked of a dental filling material—with the resulting glass having an improved ALET. The variation of the possible refractive indices encompassed by the invention is relatively wide. This glass system permits especially rational industrial production of glasses within the glass system, especially since only a defined selection of raw materials need be held in stock, within which the proportions are varied in the stated amounts. Accordingly, the procedural regimes when melting the glasses within the glass system are also very similar.

The invention claimed is:

1. Radiopaque glass comprising BaO and being free from PbO apart from impurities at most, wherein the glass has a refractive index $n_d$ in the refractive index range between 1.480 and 1.561 and has a relative aluminium equivalent thickness ALET (%) which is greater than or equal to a minimum relative aluminium equivalent thickness (min. relative ALET) which is determined by the following equation:

$$\text{min. relative ALET } (\%) = C \cdot n_d - D, \text{ where } C = 11000 \text{ and } D = 16160.$$

2. Radiopaque glass according to claim 1, comprising (in wt % based on oxide)

| | |
|---|---|
| $SiO_2$ | 35-75 |
| $B_2O_3$ | 2-16 |
| $Al_2O_3$ | 0.8-7.5 |
| $K_2O$ | 0-14 |
| BaO | 0.6-24 |
| $Cs_2O$ | 1-30 |
| $SnO_2$ | 0-15 |
| F | 0-8 |
| $BaO + Cs_2O + SnO_2 + F$ | ≥10. |

3. Radiopaque glass according to claim 2, comprising (in wt % based on oxide)

| | |
|---|---|
| $SiO_2$ | 35-75 |
| $B_2O_3$ | 4-15 |
| $Al_2O_3$ | 0.8-7.5 |
| $K_2O$ | 0-10 |
| BaO | 0.6-24 |
| $Cs_2O$ | 1-30 |
| $SnO_2$ | 0-15 |
| F | ≥0.3-8 |
| $BaO + Cs_2O + SnO_2 + F$ | ≥10. |

4. Radiopaque glass according to claim 2, comprising (in wt % based on oxide)

| | |
|---|---|
| $SiO_2$ | 35-75 |
| $B_2O_3$ | 4-15 |
| $Al_2O_3$ | 0.8-7.5 |
| $K_2O$ | 0-10 |
| BaO | 0.6-24 |
| $Cs_2O$ | 1-30 |
| $SnO_2$ | 0-15 |
| F | 0-<0.3 |
| $BaO + Cs_2O + SnO_2 + F$ | ≥10. |

5. Radiopaque glass according to claim 2, comprising F with a proportion of not more than 5.5 wt %, and/or $B_2O_3$ with a content of 5-15 wt %, and/or further comprising $La_2O_3$ with a content of 0-19 wt %.

6. Radiopaque glass according to claim 5, comprising F with a proportion of not more than 2.5 wt %, and/or $B_2O_3$ with a content of 5-15 wt %, and/or further comprising $La_2O_3$ with a content of 0-16 wt %.

7. Radiopaque glass according to claim 2, comprising (in wt % based on oxide)

| | |
|---|---|
| $SiO_2$ | 38-70 |
| $B_2O_3$ | 6-15 |
| $Al_2O_3$ | 1-7 |
| $K_2O$ | 0-7 |
| BaO | 0.8-20 |
| $Cs_2O$ | 1-28 |
| $SnO_2$ | 1-15 |
| F | 0.75-2.5 |

8. Radiopaque glass according to claim 1, comprising $Cs_2O$ in the range 1-30 wt % and optionally comprising $SnO_2$ and/or F, wherein the sum of BaO and $Cs_2O$ and $SnO_2$ and F (in wt % based on oxide) is ≥10% wt %.

9. Radiopaque glass according to claim 1, comprising $SnO_2$ and F, wherein the molar ratio of $SnO_2$ to F is 0.4-0.85.

10. Radiopaque glass according to claim 1, comprising $Cs_2O$, BaO and $SnO_2$, wherein the molar ratio of $Cs_2O$ to the sum of $Cs_2O+BaO+SnO_2$ is 0.05-0.48.

11. Radiopaque glass according to claim 1, wherein the glass, apart from impurities at most, is free from one component or more components selected from the group consisting of $Na_2O$, $Li_2O$, MgO, $CeO_2$, $TiO_2$, $La_2O_3$ and $ZrO_2$.

12. Radiopaque glass according to claim 1, wherein the glass has a relative aluminium equivalent thickness ALET (%) which is less than or equal to a maximum relative aluminium equivalent thickness (max. relative ALET) which is determined by the equation:

$$\text{max. relative ALET (\%)} = A*n_d - B, \text{ where } A=11430 \text{ and } B=16230.$$

13. Radiopaque glass according to claim 1, wherein assignment between the refractive index $n_d$ of the glass and the relative aluminium equivalent thickness ALET (%) is as follows:

| $n_d$ | ALET min. | ALET max. |
|---|---|---|
| 1.480 to <1.490 | 120% | 700% |
| 1.490 to <1.510 | 260% | 1000% |
| 1.510 to <1.530 | 520% | 1200% |
| 1.530 to <1.550 | 780% | 1500% |
| 1.550 to 1.561 | 850% | 1600% |

14. Radiopaque glass according to claim 1, wherein assignment between the refractive index $n_d$ of the glass and the relative aluminium equivalent thickness ALET (%) is as follows:

| $n_d$ | ALET min. | ALET max. |
|---|---|---|
| 1.480 to <1.490 | 120% | 760% |
| 1.490 to <1.500 | 240% | 875% |
| 1.500 to <1.510 | 360% | 990% |
| 1.510 to <1.520 | 475% | 1105% |
| 1.520 to <1.530 | 590% | 1220% |
| 1.530 to <1.540 | 705% | 1335% |
| 1.540 to <1.550 | 820% | 1450% |
| 1.550 to 1.561 | 935% | 1565% |

15. A dental glass comprising the radiopaque glass of claim 1.

16. A radiopacifier in a polymer-based dental composition, an element for optical applications, a cover glass and/or substrate glass in display technology or photovoltaics, a glass in X-ray tubes, or a material for embedding radioactive materials, comprising the radiopaque glass of claim 1.

17. Radiopaque glass according to claim 1, wherein the BaO has a content of 0.6-24 in wt% based on oxide.

18. Radiopaque glass according to claim 1, wherein a sum of BaO+Cs2O+SnO2+F is >14 wt.% based on oxide.

* * * * *